United States Patent [19]
Shiono et al.

[11] Patent Number: 5,919,917
[45] Date of Patent: Jul. 6, 1999

[54] PHOTOCLEAVABLE CIRCULAR OLIGONUCLEOTIDES

[75] Inventors: Hirofumi Shiono; Hirofumi Kodama, both of Shizuoka; Makiko Kojima, Nagano, all of Japan

[73] Assignee: Laboratory of Molecular Biophotonics, Shizuoka, Japan

[21] Appl. No.: 09/011,551

[22] PCT Filed: Jun. 9, 1997

[86] PCT No.: PCT/JP97/01959

§ 371 Date: Mar. 2, 1998

§ 102(e) Date: Mar. 2, 1998

[87] PCT Pub. No.: WO97/47639

PCT Pub. Date: Dec. 18, 1997

[30] Foreign Application Priority Data

Jun. 10, 1996 [JP] Japan ..................................... 8-170632

[51] Int. Cl.$^6$ ............................... C07H 21/04; C12Q 1/68
[52] U.S. Cl. .............................. 536/23.1; 435/6; 536/22.1
[58] Field of Search ........................... 435/6, 91.1, 172.3, 435/320.1, 325, 375, 410, 243; 536/23.1, 24.3, 24.5, 25.3, 22.1; 514/44

[56] References Cited

U.S. PATENT DOCUMENTS

| | | | |
|---|---|---|---|
| 5,258,506 | 11/1993 | Urdea et al. ............................. | 536/23.1 |
| 5,430,136 | 7/1995 | Urdea et al. ............................... | 536/27 |
| 5,683,874 | 11/1997 | Kool ........................................... | 435/6 |

FOREIGN PATENT DOCUMENTS

| | | |
|---|---|---|
| 0 642 798 A2 | 3/1995 | European Pat. Off. . |
| 0 693 287 A1 | 1/1996 | European Pat. Off. . |
| 2675803 | 10/1992 | France . |
| WO 92/02528 | 2/1992 | WIPO . |

OTHER PUBLICATIONS

Condorelli et al., *Photochemistry and Photobiology,* 62 (1), 155–161 (1995).
Cosstick et al., *Biochemistry,* 24, 3630–3638 (1985).
De Clerq et a., *Science,* 165, 1137–1139 (1969).
De Napoli et al., *Gazzetta Chimica Italiana,* 121, 505–508 (1991).
Miller et al., *Biochemistry,* 18 (23), 5134–5143 (1979).
Ordoukhanian et al., *J. Am. Chem. Soc.,* 117, 9570–9571 (1995).
Piette, *Reunion D'Anvers* (Societe Belge de Biophysique), 1050–1051 (Jun. 1, 1979).
Prakash et al., *J. Chem. Soc., Chem. Commun.,* 1161–1163 (1991).
Puttarju et al., *Nucleic Acids Research,* 21 (18), 4253–4258 (1993).
Wickstrom, *J. Biochem. Biophys. Methods,* 13, 97–102 (1986).
Zamecnik et al., *Proc. Natl. Acad. Sci. USA,* 75 (1), 280–284 (1978).

*Primary Examiner*—John L. LeGuyader
*Assistant Examiner*—Mark L. Shibuya
*Attorney, Agent, or Firm*—Leydig, Voit & Mayer, Ltd.

[57] ABSTRACT

The photocleavable cyclic oligonucleotide according to the invention is the one that possesses a base sequence having the hybridization ability toward DNA or RNA to targeted, and is further provided with the structure cyclized by a photocleavable group. Accordingly, the photocleavable cyclic oligonucleotide according to the invention, after having been introduced in vivo, is hardly susceptible to the nuclease decomposition reaction owing to its cyclic structure and thus it is capable of diffusing toward the predetermined sites in vivo with sufficient time. Moreover, by being irradiated with the light at an appropriate wavelength after a predetermined period of time, the photocleavable group as described above is cleaved photochemically, thus cutting the predetermined bond. This permits the oligonucleotide that was cyclic to be a linear oligonucleotide which expresses the function of an antisense oligonucleotide.

11 Claims, 18 Drawing Sheets

… … …

PHOTOCLEAVABLE CIRCULAR OLIGONUCLEOTIDES

CROSS REFERENCE TO RELATED APPLICATIONS

This is a national stage application according to 35 U.S.C. §371 of PCT/JP97/01959, filed Jun. 9, 1997.

TECHNICAL FIELD

This invention relates to oligonucleotide that has been cyclized by photocleavable groups.

BACKGROUND ART

Oligonucleotides are known to be very important, useful substances in the field of biology and medical science: as probes that recognize and detect specific sequences in the detection of nucleic acids; as primers for the use in PCR method which is an essential technique in genetic engineering; and further as antisense oligonucleotides for the use in the antisense method which is actively researched in recent years in the field of gene therapy.

In order for the aforementioned antisense oligonucleotides to manifest their respective functions, they all need the ability of their base sequence moiety to hybridize with complementary base sequences—what is known as "hybridization ability".

Further, it is required that the aforementioned antisense oligonucleotides possess not only the hybridization ability, but also the stability in vivo. For example, some attempts have been made concerning the control of genetic information by the use of antisense oligonucleotides. See, Zamecnick, Stephenson et al., Proc. Natl. Acad. Sci., U.S.A., 75, 280–284 (1978). The oligonucleotides which are used for this purpose are normally derived from nature and many of them have only, extremely low resistance to nuclease. This presents a problem that they are susceptible to undesired decomposition reactions in vivo. Consequently, a variety of such modified oligonucleotides that remedy these drawbacks are actually being developed.

One such example is an oligonucleotide with a phosphorothioate bond, which is referred to as "S-Oligo" (DeClercq et al., Science, 165, 1137–1139 (1969)), and it can be easily synthesized on a DNA auto-synthesizer. It is known that this kind of oligonucleotides have substantial resistance to nuclease. See, Wickstrom et al., J. Biol. Biophys. Meth., 13, 97–102 (1986). Another example is an oligonucleotide with a methylphosphonate bond, which is referred to as "MP-Oligo" (Miller et al., Biochemistry, 18, 5134–5142 (1979)). Substitution of one of the oxygen atoms present in phosphoric ester bonds of DNA of the natural type with a methyl group provides the nucleotide with resistance to nuclease, and in addition, it eliminates a charge at the phosphoric acid moiety, thus substantially improving membrane permeability.

However, the aforementioned S-Oligo is a racemic mixture including many isomers with their chiral centers at phosphoric ester bond moieties, and has a drawback in that it is provided with a low affinity to RNA or DNA. A further drawback is that it does not possess sufficient stability in vivo (i.e., resistance to nuclease).

Also, the MP-Oligo is a racemic mixture like the S-Oligo, and has a drawback in that it is provided with a low affinity to RNA or DNA. A further drawback is that its water solubility is low because there is no charge at the phosphoric ester bond moieties.

Furthermore, the still further drawback of the antisense oligonucleotides known in the art is that once they have been introduced in vivo, they can not be controlled with regard to the expression of their activities such as concentrations, sites, and time.

DISCLOSURE OF INVENTION

Figure 1:
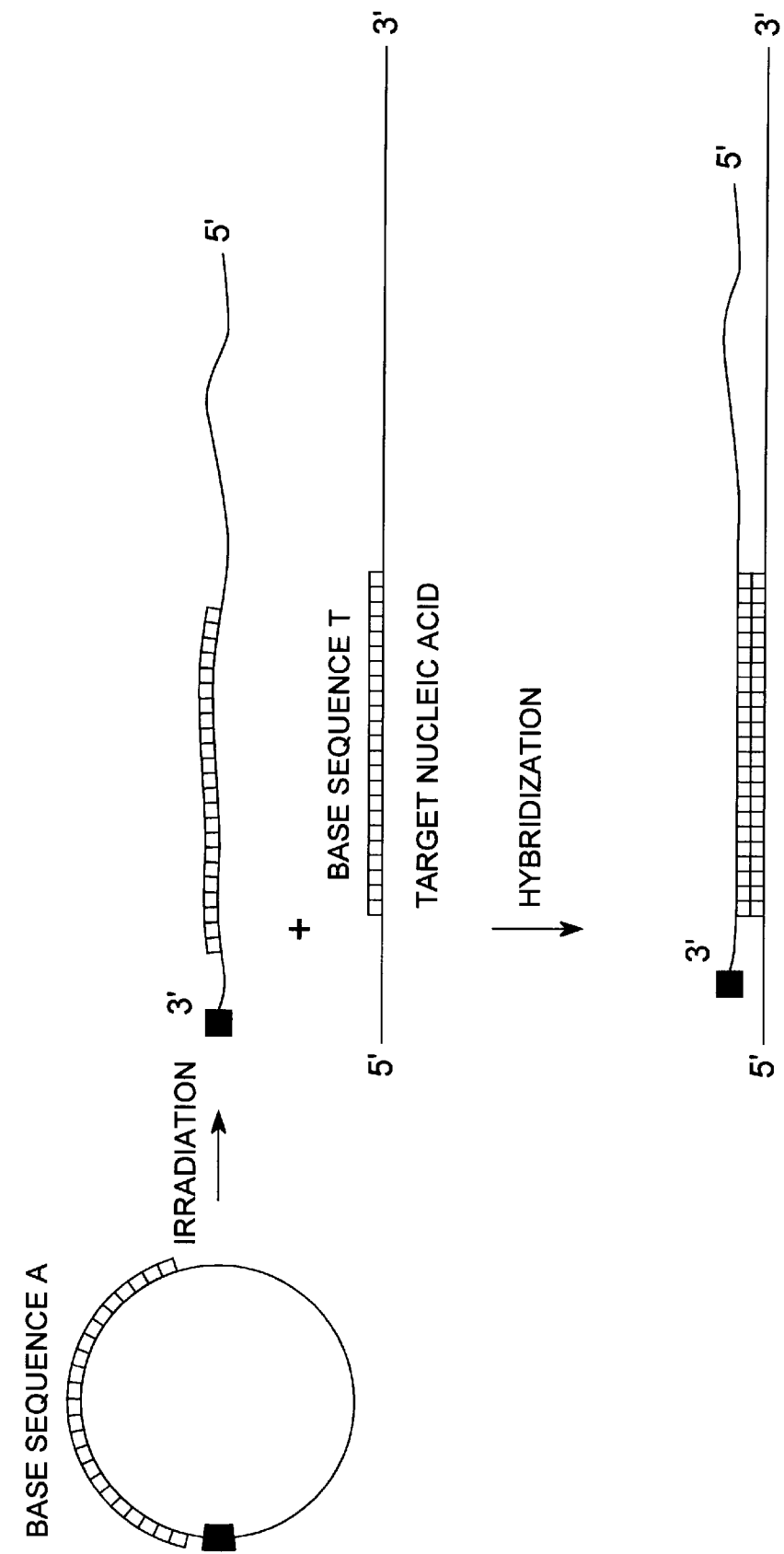
FIG. 1 illustrates an embodiment of photocleavable cyclic oligonucleotides according to this invention, where the black square represents a photocleavable group and Base Sequence A represents a base sequence that can be hybridized with target Base Sequence T.

This invention has been made in consideration of the drawbacks as described above that are inherent in the modified antisense oligonucleotides in the prior art. The present inventors have discovered antisense oligonucleotides having novel structures which possess sufficiently high affinities to RNA or DNA and in addition are provided with sufficient resistance to nuclease in vivo and which remedy the drawbacks, and have accomplished the invention.

Specifically, a photocleavable cyclic oligonucleotide according to the invention is the one that hybridizes with DNA or RNA to be targeted, and is further provided with a structure cyclized by a photocleavable group. As used herein, the term, "photocleavable group" means a group having a moiety known as a photocaged reagent in the art, wherein specific bonds can be cleaved by irradiation at specific wavelengths.

Accordingly, the photocleavable cyclic oligonucleotide according to the invention, after having been introduced in vivo, is not susceptible to nuclease decomposition reaction owing to its cyclic structure and is capable of diffusing toward the predetermined sites in vivo with sufficient time. Furthermore, the aforementioned photocleavable group decomposes photochemically, after a predetermined period of time, upon irradiation at an appropriate wavelength and the specific bond is cleaved to transform the oligonucleotide with a cyclic structure into a linear oligonucleotide, which enables the oligonucleotide to hybridize with RNA or DNA to be targeted.

In addition, after the photocleavable cyclic oligonucleotide has diffused into a region where the target DNA or target RNA is present, it forms a complex by interacting with a partial base sequence of the target DNA or target RNA and, upon irradiation, decomposes photochemically to become linear, which can effectively bring out its activity as an antisense oligonucleotide.

More specifically, this invention provides a cyclic oligonucleotide comprising at least one photocleavable group, wherein the oligonucleotide is intramolecularly bonded by the photocleavable group.

Also, the invention provides the cyclic oligonucleotide as described above wherein the photocleavable group has the following structure:

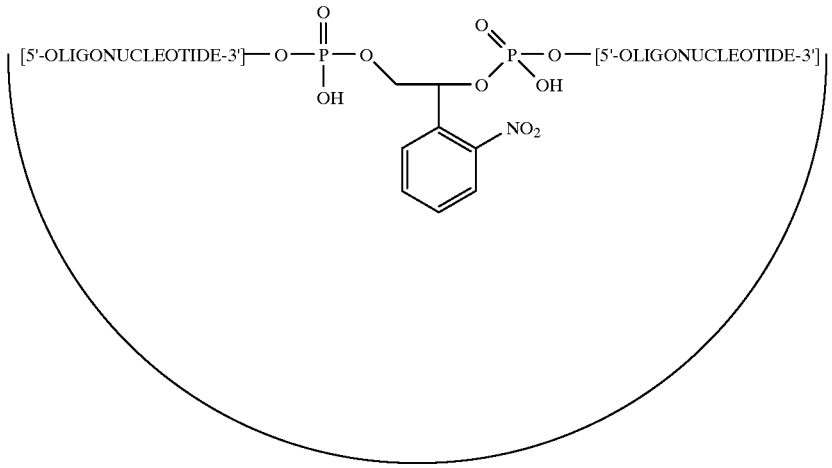

Further, the invention provides the cyclic oligonucleotide as described above wherein the photocleavable group has the following structure:

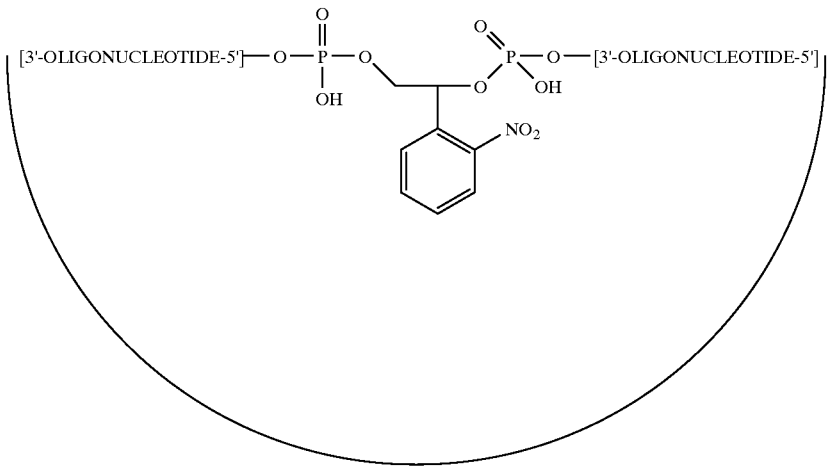

Also, the invention provides the cyclic oligonucleotide as described above wherein the oligonucleotide comprises from 10 to 200 bases.

Also, the invention provides the cyclic oligonucleotide as described above wherein the oligonucleotide comprises from 30 to 100 bases.

Still further, the invention provides the cyclic oligonucleotide as described above wherein the oligonucleotide is provided with a first base sequence capable of hybridizing with at least a partial base sequence of a target nucleic acid upon cleavage of the photocleavable group.

Also, the invention provides the cyclic oligonucleotide as described above wherein the oligonucleotide is provided with a first base sequence capable of hybridizing with at least a partial base sequence of a target nucleic acid upon cleavage of the photocleavable group and with a second base sequence through which the oligonucleotide forms a complex with the target nucleic acid.

BEST MODE FOR CARRYING OUT THE INVENTION

The photocleavable cyclic oligonucleotide according to this invention is an oligonucleotide which has a structure cyclized by at least one photocleavable group. Further, the base sequence of the photocleavable cyclic oligonucleotide according to the invention has in its part a base sequence capable of hybridizing with a nucleic acid to be targeted (DNA, RNA or the like) in a complementary manner. In addition, the photocleavable cyclic oligonucleotide according to the invention has in its part a base sequence capable of forming a complex with the nucleic acid to be targeted.

Figure 2:
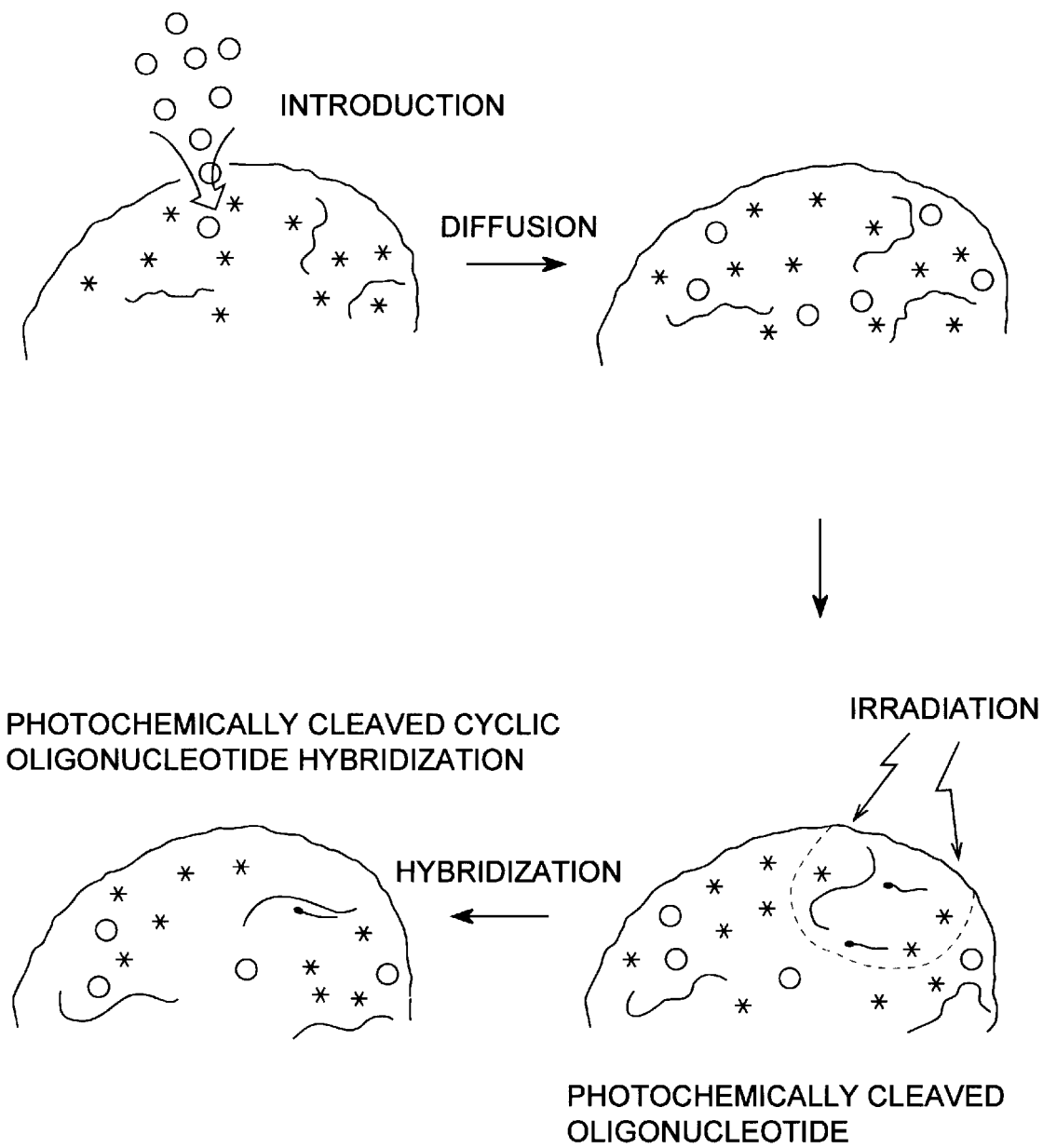
FIG. 2 illustrates the manner in which after the photocleavable cyclic oligonucleotides according to the invention as shown in FIG. 1 (which are represented by small circles) have been introduced into cells and diffused, a portion of the cells is irradiated to cause cleavage of the photocleavable groups and the oligonucleotides are converted to linear oligonucleotides which then hybridize with target DNAs to express antisens activities.

A preferred embodiment of the photocleavable cyclic oligonucleotides according to the invention is an oligonucleotide which has the structure schematically shown in FIG. 1 and which includes a specific base sequence cyclized by the photocleavable group: the base sequence is made linear after the photocleavage and is able to hybridize with the target nucleic acid as an antisense oligonucleotide, and it is represented as Base Sequence A in FIG. 1. As shown in FIG. 2, when the photocleavable cyclic oligonucleotide according to the invention is introduced into the region where the target nucleic acids are present, it is resistant to a variety of nuclease by virtue of its cyclic structure and can diffuse sufficiently close to the target nucleic acid without being subjected to hydrolysis. Moreover, by being irradiated with the light of desired intensity at desired sites and times, the photocleavable group of the photocleavable cyclic oligonucleotide according to the invention is cleaved to provide a linear oligonucleotide. Such linear oligonucleotide can hybridize with the specific base sequence of the target nucleic acid present in its vicinity, which allows it to exhibit the function of an anitisens-oligonucleotide. Simultaneously, the linear oligonucleotide that does not hybridize with the target nucleic acid is rapidly hydrolyzed by the nuclease present in the vicinity.

Figure 3:
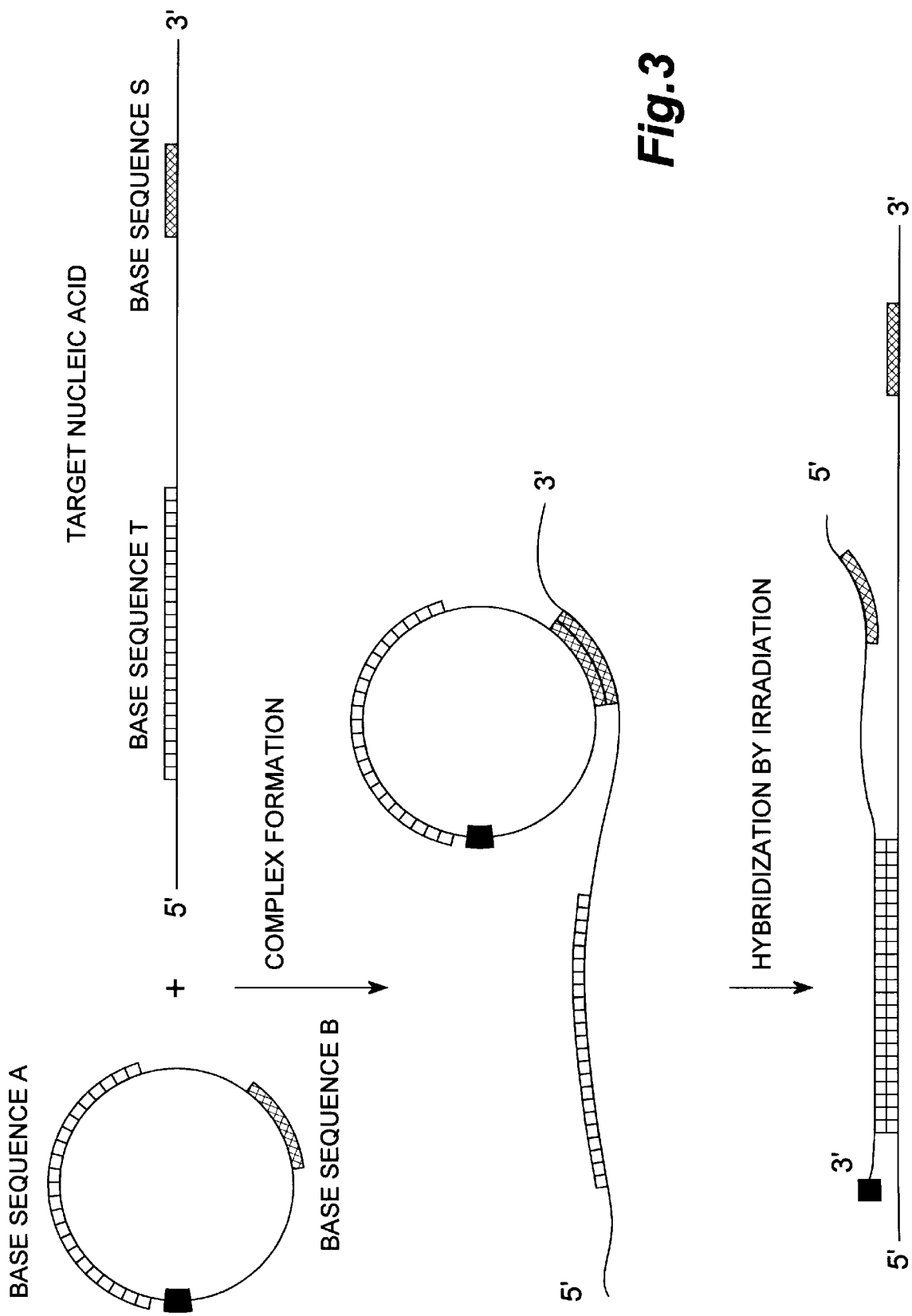
FIG. 3 illustrates an embodiment of photocleavable cyclic oligonucleotides according to the invention, where the black square represents a photocleavable group, Base Sequence A represents a base sequence that can be hybridized with target Base Sequence T, and Base Sequence B represents a base sequence that can mutually interact with target Base Sequence S.
Figure 4:
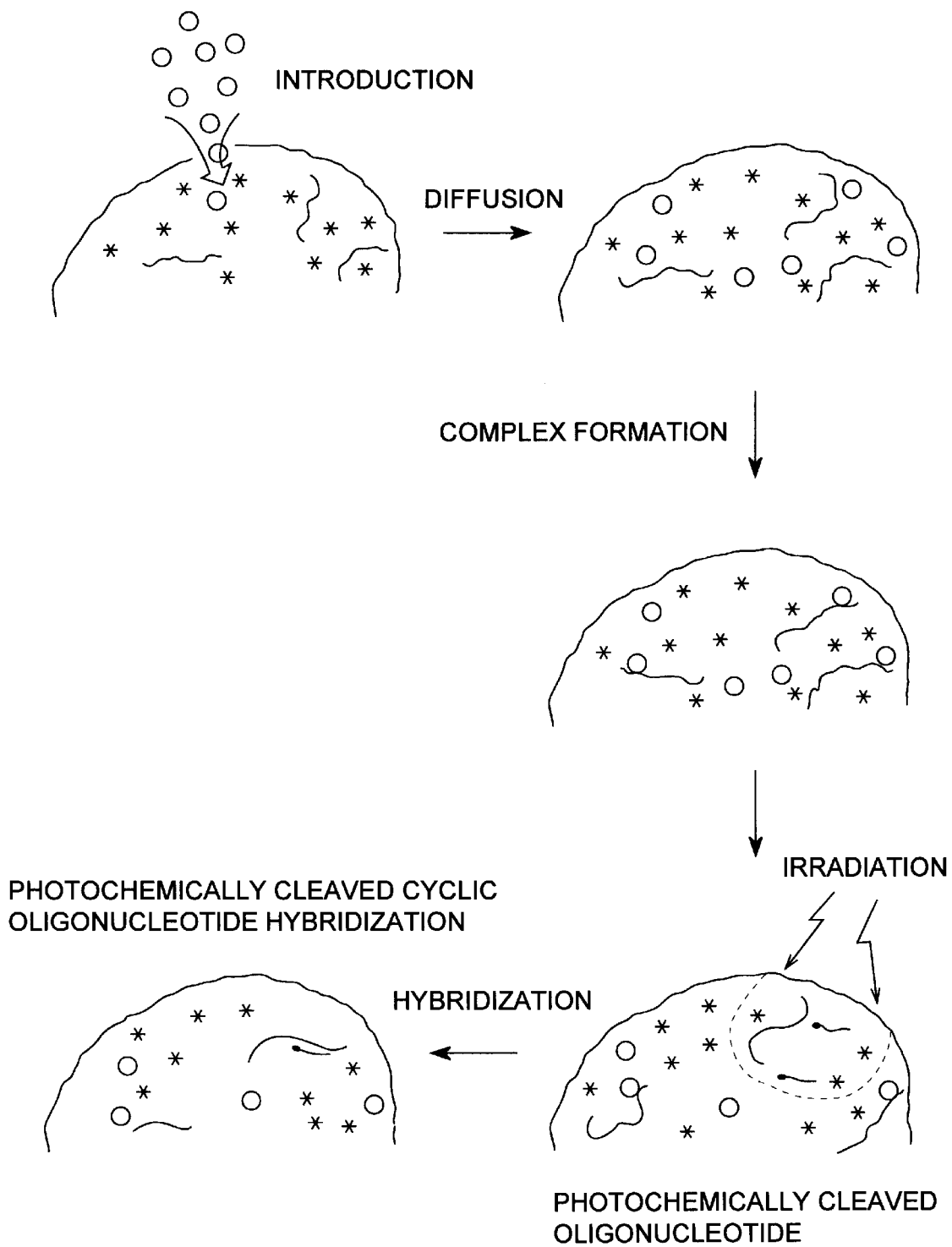
FIG. 4 illustrates the manner in which after the photocleavable cyclic oligonucleotides according to the invention as shown in FIG. 3 (which are represented by small circles) have been introduced into cells and diffused, they interact with target nucleic acids to form complexes and further a portion of the cells is irradiated to cause cleavage of the photocleavable groups and the oligonucleotides are converted to linear oligonucleotides which then hybridize with target DNAs to express antisens activities.

As schematically shown in FIG. 3, another preferred structural example of the photocleavable cyclic oligonucleotides according to the invention is an oligonucleotide which has a specific base sequence cyclized by the photocleavable group and a base sequence capable of interacting with a target nucleic acid in the cyclized form: the former base sequence is made linear after the photocleavage and is able to hybridize with the target nucleic acid as an antisense oligonucleotide, and it is represented as Base Sequence A in FIG. 3; and the latter base sequence is represented as Base Sequence B in FIG. 3. As shown in FIG. 4, when the photocleavable cyclic oligonucleotide according to the invention is introduced into the region where the target nucleic acids are present, it is resistant to a variety of nuclease by virtue of its cyclic structure and can diffuse sufficiently close to the target nucleic acid without being subjected to hydrolysis, further allowing the formation of a complex by the interaction with a portion of the target nucleic acid (represented as Base Sequence S in FIG. 3). In this case, by being irradiated with the light of desired intensity at desired sites and times, the photocleavable group of the photocleavable cyclic oligonucleotide according to the invention is cleaved to provide a linear oligonucleotide. Such linear oligonucleotide can hybridize with the specific base sequence of the target nucleic acid present in its vicinity, which allows it to effectively exhibit the function of an anitisens-oligonucleotide. There is no particular limitation to the kind of Base Sequence B which can interact as described above, as well as to its base number, but it is preferred that Sequence B has a longer sequence than Base Sequence A.

The structural characteristics of the photocleavable cyclic oligonucleotides according to the invention will be explained hereinafter.

Photocleavable Groups

The photocleavable cyclic oligonucleotide according to the invention is the one that has a photocleavable group within its molecule. Such photocleavable group is the one that is photochemically cleaved by irradiation to render its cyclic structure linear as a result, and thus manifests the activity of an antisense oligonucleotide. See FIGS. 1 and 3.

Accordingly, such photocleavable group is the one that bonds the 5'-end and the 3'-end of a linear oligonucleotide with a base sequence which should function as an antisense oligonucleotide, to form a cyclic structure wherein at least one part of the bond is to be cleaved under irradiation. Therefore, the structures that can be used for this purpose are not particularly limited in this invention and they may be any functional groups having the aforementioned properties. For example, a functional group that is conventionally known as a photocaged reagent is one such kind which can preferably be used. In the invention, the functional group is more preferably the one that forms a phosphoric ester bond.

Furthermore, it is required that the photocleavable group having the aforementioned functional group be equipped with a functional group to be taken in the molecule by the method using a standard DNA/RNA autosynthesizer (e.g., on the basis of the phosphoramidite method). For example, groups of the nitrobenzyl type with the following structures can preferably be used for the photocleavable group which has the aforementioned two functions.

Figure 5:
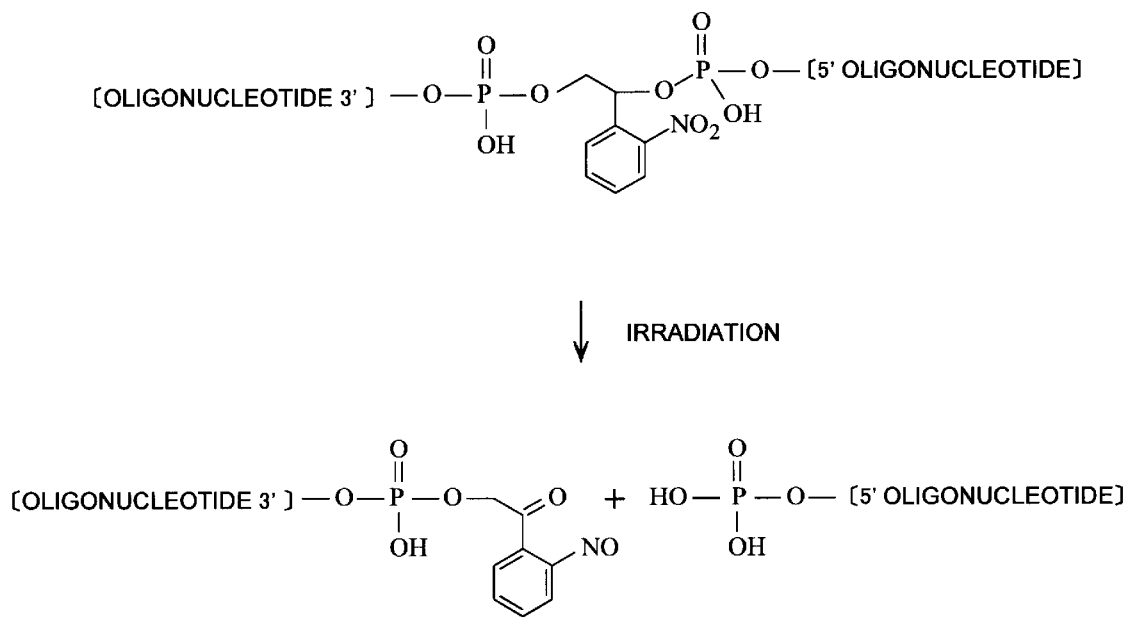
FIG. 5 illustrates the manner in which two kinds of oligonucleotides are bonded through a phosphoric ester group by a photocleavable group of nitrobenzyl type and the bond, upon irradiation, gives rise to a phosphoric acid group and a nitrosophenyl derivative.
Figure 6:
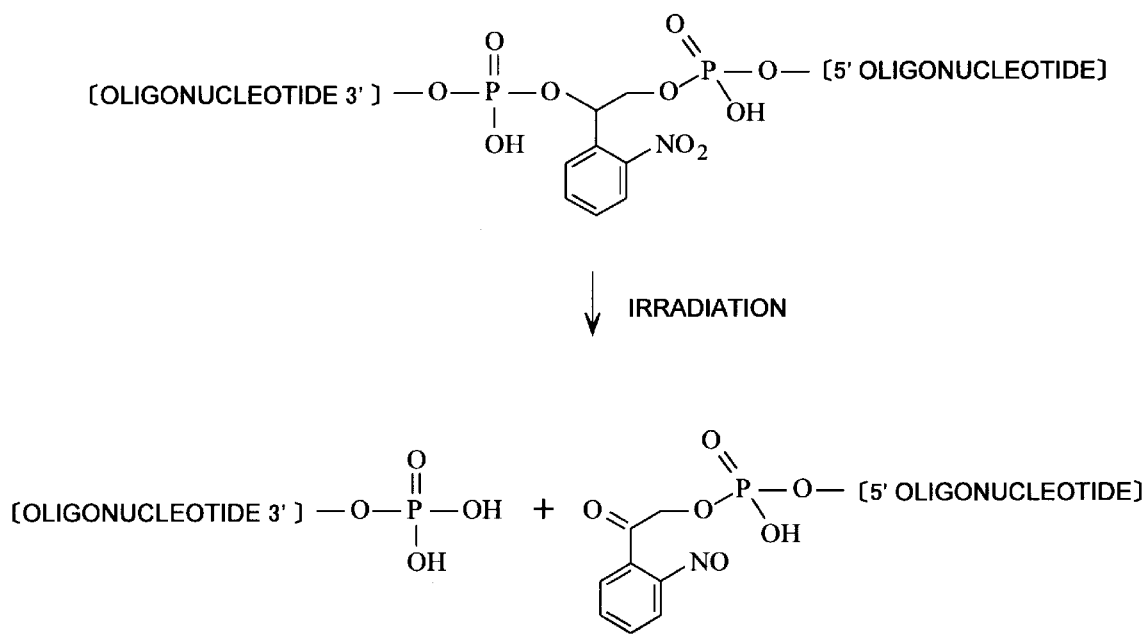
FIG. 6 illustrates the manner in which two kinds of oligonucleotides are bonded through a phosphoric ester group by a photocleavable group of nitrophenyl type and the bond upon irradiation, gives rise to a phosphoric acid group and a nitrosophenyl derivative.

As shown in FIGS. 5 and 6, it is recognized that one of the phosphoric ester bonds of this structure is cleaved selectively when it is subjected to irradiation at an appropriate wavelength and the structure is split into a phosphoric acid portion and a portion with a nitrosophenyl derivative.

Thus, in order to introduce into an arbitrary site of the oligonucleotide, the photocleavable group of the nitrobenzyl type shown in FIGS. 5 and 6 using the phosphoramidite method, phosphoramidite reagents with the following structures can, for example, be used.

Figure 7:
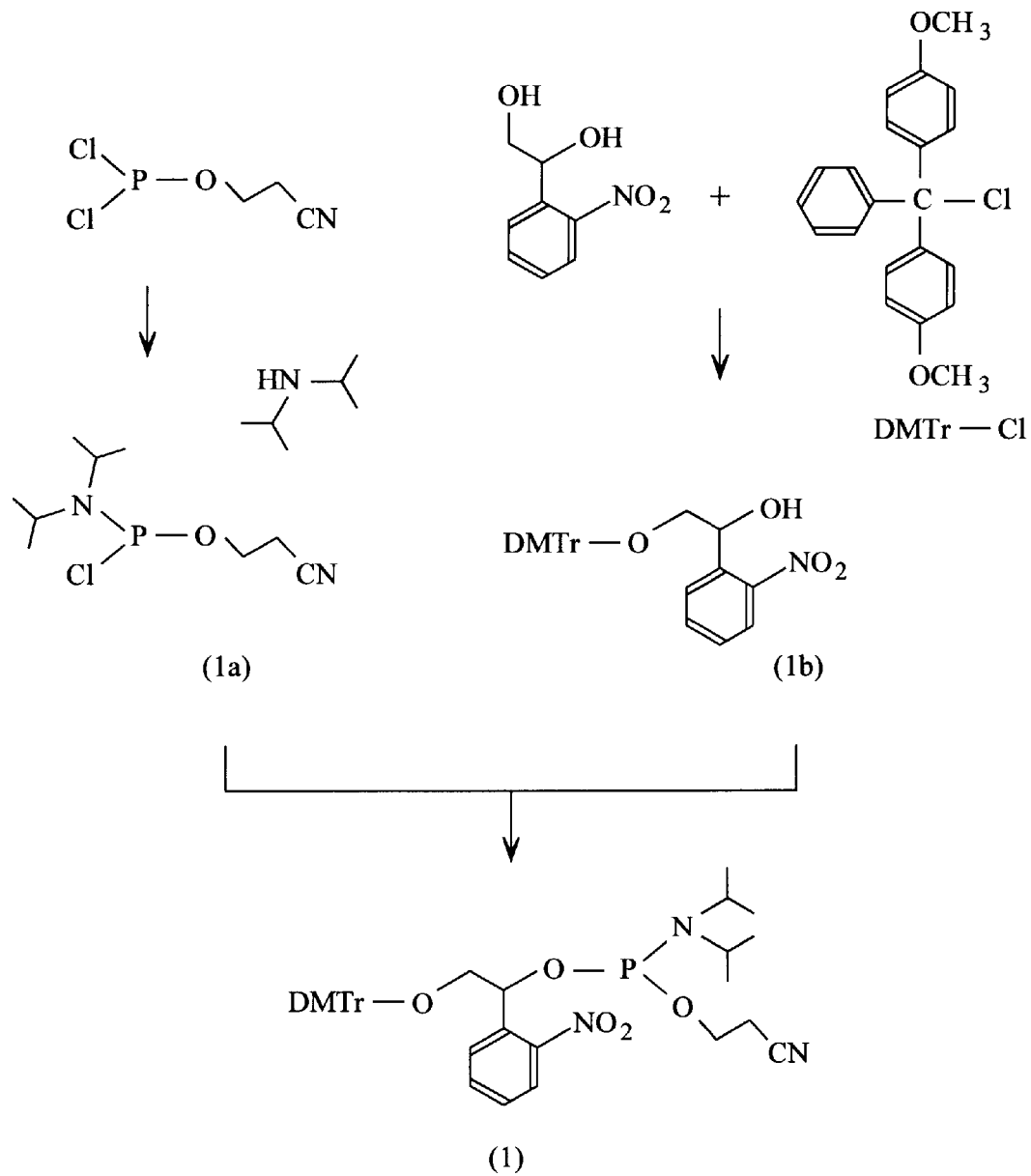
FIG. 7 illustrates an embodiment of the schemes by which a phosphoamidite reagent according to the invention is synthesized.
Figure 8:
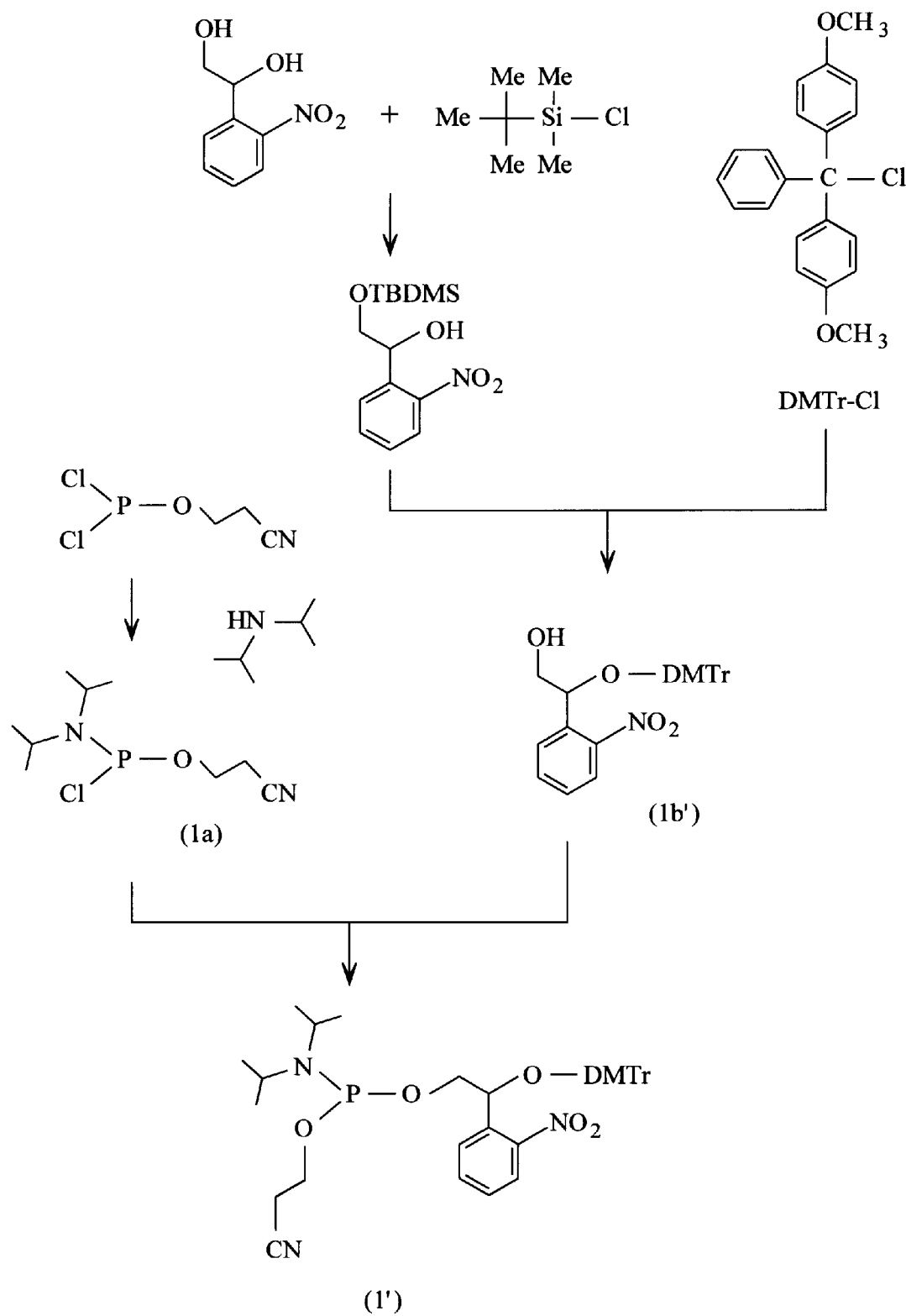
FIG. 8 illustrates another embodiment of the schemes by which a different phosphoamidite reagent according to the invention is synthesized.

These reagents can respectively be prepared according to the synthetic methods shown in FIGS. 7 and 8, for example. Specifically, a phosphoramidite reagent (1) [1-(o-nitrophenyl)-2-dimethoxytrityloxy]ethoxy-N,N-diisopropylamino-2-cyanoethoxyphosphine) can be synthesized by the reaction between (3-chloro-N,N-diisopropylamino-(2-cyanoethoxy)phosphine (1a) and (1-O-dimethoxytrityl-2-(o-nitrophenyl)-1,2-ethanediol (1b). Similarly, (1') can be synthesized by the method shown in EXAMPLES.

The phosphoramidite reagents thus obtained are usable without further purification as a reagent for DNA/RNA autosynthesizer employing the phosphoramidite method.

Cyclic Oligonucleotides

The base sequence for the cyclic oligonucleotide according to this invention is not limited. While the molecule is cleaved photochemically at its site that is a photocleavable group which is to be introduced into this oligonucletide and provides a linear oligonucleotide, the base sequence can arbitrarily be selected such that once it has been cleaved in a manner set forth, it is able to hybridize with RNA or DNA to be targeted (target nucleic acids) and to function as an antisense-oligonucleotide.

Furthermore, the cyclic oligonucleotide contains a base sequence capable of interacting with the target nucleic acid and forming a complex while retaining a cyclic structure. Such base sequence is the one that is complementary to a partial base sequence of the target nucleic acid and may contain the number of bases which enables interaction such as hybridization. The kind and number of such base sequence can appropriately be selected, but the number is preferably from 10 to 200 bases, more preferably from 30 to 100 bases. In cases where the base number is within the aforementioned range, the base sequence contains an oligonucleotide portion with 15–30 bases which normally can be used as an antisense oligonucleotide and, if necessary, it becomes possible to synthesize a cyclic photocleavable oligonucleotide having a base portion capable of interacting with the target nucleic acid.

Further, although not particularly limited thereto, the bonding by the action of ligase is preferably used to cyclize the linear oligonucleotide obtained as described above (which may or may not contain the photocleavable group). To this end, the 5'-end is phosphorylated and then the cyclization is enabled by conducting a conventional ligase reaction using an appropriate template. In this instance, the preparation of an oligonucleotide that serves as the template for the ligase reaction can readily be carried out using a standard autosynthesizer or the like.

Although there is also no particular limitation to the ligase reaction, the use of the template oligonucleotide bonded with biotin makes aftertreatment easy.

Figure 9:
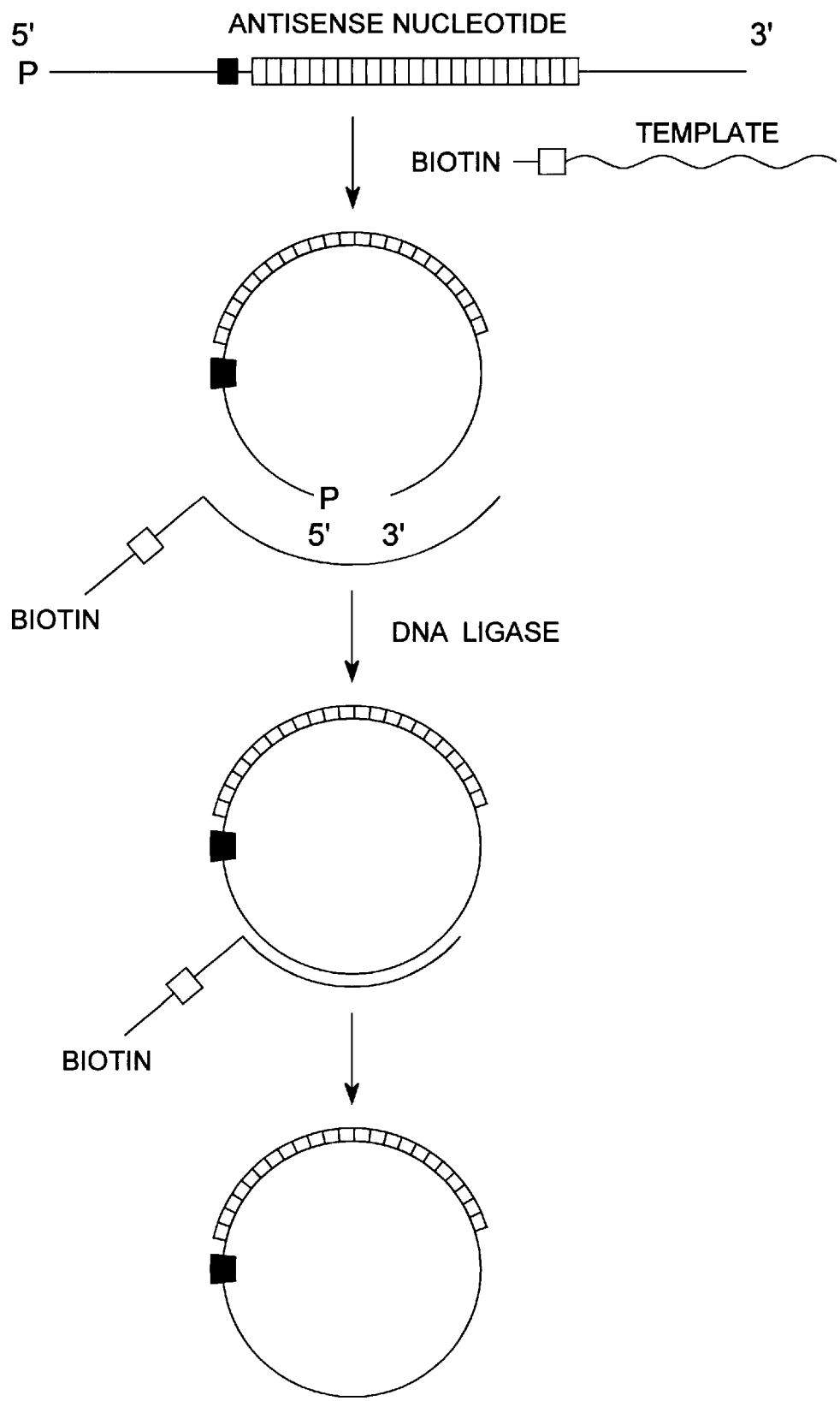
FIG. 9 illustrates an embodiment of the preparation methods for the photocleavable cyclic oligonucleotides according to the invention, where an oligonucleotide having a photocleavable group introduced therein with its 5'-end phosphorylated is allowed to hybridize with a template oligonucleotide having biotin bonded and is then cyclized by DNA ligase reaction.

FIG. 9 illustrates an embodiment of the preparation of the cyclic oligonucleotides according to the invention.

Also, in the synthesis of a short oligonucleotide, other methods are employable, for example, where an oligonucleotide with its 5'-end phosphorylated and a template are provided to form a triple-strand and it is then cyclized with BrCN-imidazole. See, Prakash, G. and Kool, E. T., J. Chem. Soc., Chem. Commun., (1991) 1161–1163.

In addition, it is possible to synthesize the cyclic oilgonucleotides according to the solid phase method. See, Napoli, L. D., Montesarchio, D., Piccialli, G., Satacroce, C., Mayol, L., Galenone, A., Messere, A., Gazetta Chimica Italiana 121 (1991) 505–508.

Photocleavage Reaction

There is no particular limitation to the photocleavage reaction of the cyclic oligonucleotide having a photocleavable group according to the invention. For example, in the case of a functional group of the nitrobenzyl type, conditions such as the wavelength and intensity of the light to be irradiated are well known in the art and those conditions are usable without any significant changes.

Furthermore, the whole sample may be irradiated with irradiation light, or a portion of the sample may be narrowly irradiated. When the specific site of a portion of the sample is narrowly irradiated, the antisense activity only manifests at the specific site as illustrated in FIG. 2 or FIG. 4.

EXAMPLES

Although this invention is concretely illustrated by way of examples, it is not limited to the following examples insofar as it does not depart from its essence.

Synthesis of 3-Chloro-N,N-diisopropylamino-(2-cyanoethoxy)phosphine (1a)

3-Dichloro-(2-cyanoethoxy)phoshine 27 g was dissolved in 80 ml of anhydrous diethyl ether under the nitrogen atmosphere in a reactor fitted with a nitrogen gas inlet tube, magnetic stirrer, and dropping funnel and it was cooled to −15° C. To this was slowly added in dropwise 31 g of diisopropylamine dissolved in 30 ml of anhydrous diethyl ether under sufficient stirring. After stirring for 18 hours, diisopropylamine hydrochloride which had precipitated was filtered off.

After removal of the solvent under reduced pressure, the crude product was obtained as a light yellowish transparent oily substance. This was separated and purified by distillation under reduced pressure (108–115° C./0.1 mmHg) (22 g;

the purity was greater than 95% based on gaschromatography). Structural analysis by ¹HNMR (JEOL JNM-PMX60, in deuteriochloroform): δ 3.6–4.2 (4H, m, ethylene of the cyanoethoxy group); 2.9 (2H, t, methine of the isopropyl group); 1.3 (12H, d, methyl of the isopropyl group).

Dimethoxytritylation of o-Nitrophenyl-1,2-ethanediol

A reactor in which a 100 ml flask had been fitted with a magnetic stirrer and dropping funnel was charged with 2.5 g of o-nitrophenyl-1,2-ethanediol and 50 ml of anhydrous pyridine. To this was added 4.6 g of dimethoxytrityl chloride under cooling at 5° C. After allowing to react for 18 hours under stirring, a majority of pyridine was removed under reduced pressure and 100 ml of ethyl acetate and 100 ml of saturated brine were added to the residue. The organic solvent layer was washed with an aqueous saturated sodium bicarbonate solution and saturated brine, dried over sodium sulfate, and the solvent was removed under reduced pressure to give 6.7 g of a red oily substance. The resulting crude product was purified with a silica gel column chromatograph (chloroform eluent containing 0.5% triethylamine) and 6.0 g of the desired product, 1-O-dimethoxytrityl-2-(o-nitrophenyl)-1,2-ethanediol) (1b) was obtained. Structural analysis by ¹HNMR (JEOL JNM-PMX60, in deuteriochloroform): δ 6.9–8.1 (17H, m, phenyl of the dimethoxytrityl, phenyl of the nitrophenyl); 4.0 (6H, s, methoxy of the dimethoxyphenyl); 3.8 (1H, t, methine); 3.4 (2H, d, methylene).

Synthesis of [1-(o-Nitrophenyl)-2-dimethoxytrityloxy]ethoxy-N,N-diisopropylamino-2-cyanoethoxyphosphine (1)

1-O-Dimethoxytrityl-2-(o-nitrophenyl)-1,2-ethanediol thus obtained above 6.0 g and 3.1 g of triethylamine was dissolved in 50 ml of anhydrous dichloromethane and to the solution was added dropwise 3.6 g of 3-chloro-N,N-diisopropylamino-(2-cyanoethoxy)phosphine dissolved in 10 ml of anhydrous dichloromethane under cooling at 5° C. After allowing to react for 1 hour, 150 ml of ethyl acetate was added to the reaction solution and it was washed with saturated brine three times. The crude product which was obtained after removal of the solvent was purified with a silica gel column chromatograph (hexane/ethyl acetate 2:1 eluent containing 0.5% triethylamine) and 8.9 g of the desired product (purity of 98% as determined by reverse phase HPLC) was obtained. Structural analysis by ¹HNMR (JEOL JNM-PMX60, in deuteriochloroform): δ 6.8–8.1 (17H, m, phenyl of the dimethoxytrityl, phenyl of the nitrophenyl); 4.0 (1H, t, methine); 3.7 (6H,s, methyl of the dimethoxyphenyl); 3.3–3.6 (6H, m, methylene of the cyanoethoxy group, methylene of the nitrophenylethanediol); 2.3 (2H, t, methine of the isopropyl group); 1.2 (12H, d, methyl of the isopropyl group). Molecular weight: (TOF-MS): 669.30; Calcd.: 669.76.

tert-Butyldimethylsilylation of o-Nitrophenyl-1,2-ethanediol

A reactor fitted with a magnetic stirrer was charged with 100 ml of dichloromethane, 10 ml of trimethylamine, 5 mg of dimethylaminopyridine, and 10.0 g of o-nitrophenyl-1,2-ethanediol under the nitrogen atmosphere in a dark room and the reagents were mixed. The resulting solution was cooled to 5° C. tert-Butyldimethylsilylchloride 9.8 g was then added in several portions to the solution and it was stirred for about 3 hours. The end point of the reaction was monitored by TLC and the reaction was determined to be complete when the disappearance of the starting materials was observed. The purity of the reaction product was confirmed on a TLC and the product was used in the next step without further purification.

Dimethoxytritylation of (1-O-tert-Butyldimethylsilyl-2-(o-nitrophenyl)-1,2-ethanediol)

Trimethylamine 10 ml was added to the aforementioned reaction solution as obtained and then 18.6 g of dimethoxytritylchloride was added in several portions at room temperature. As such, stirring continued overnight and the completion of the reaction was confirmed by TLC. The solvent was removed under reduced pressure and to the resulting residue was added 200 ml of ethyl acetate. The solution was further washed thoroughly with water and saturated brine and the solvent was removed under reduced pressure to give 21 g of an oily substance. The thus obtained residue was purified by silica gel column chromatography using chloroform as an eluent and 22.0 g of an oily substance was obtained. Structural analysis by ¹HNMR (JEOL JNM-PMX60, in deuteriochloroform as δ (ppm)): 6.6–7.8 (17H, m, phenyl of the dimethoxytrityl group, phenyl of the nitrophenyl); 5.5 (1H, t, methine); 3.9 (2H,d, methylene); 3.8 (6H, s, methyl of the dimethoxymethy group); 1.0 (9H, s, tert-butyl of the tert-butyldimethylsilyl group); 0.1 (6H, s, methyl of the tert-butyldimethylsilyl group).

Elimination of tert-butyldimethylsilyl group of 1-O-tert-Butyldimethylsilyl-2-O-dimethoxytrityl-2-(o-nitrophenyl)-1,2-ethanediol A reactor fitted with a magnetic stirrer was charged with 21 g of 1-O-tert-butyldimethylsiliyl-2-dimethoxytrityl-2-(o-nitrophenyl)-1,2-ethanediol and 100 ml of tetrahedrofuran at room temperature and to the solution was added 2.6 g of tetrabutylammonium fluoride in several portions under vigorous stirring. As such, stirring continued for about 1 hour and after the completion of the reaction was confirmed by TLC, the reaction solution was concentrated to terminate the reaction. Ethyl acetate was added to the residue and the solution was washed with water and saturated brine. After drying, the solvent was removed under reduced pressure to give 18 g of an oily residue. This residue was purified with a silica gel column chromatograph employing chloroform as an eluent, affording 16.0 g of an oily product.

[2-Dimethoxytrityloxy-2-(o-nitrophenyl)]-ethoxy-N,N-diisopropylamino-2-cyanoethoxyphosphine (1')

A reactor fitted with a magnetic stirrer was charged with 100 ml of dichloromethane, 7.0 g of triethylamine, 16.0 g of 1-dimethoxytrityl-1-(o-nitrophenyl)-1,2-ethanediol in a dark room and to this was added in dropwise a solution of 3-chloro-N,N-diisopropylamino-2-cyanoethoxyphosphine 8.5 g in dichloromethane at room temperature. The reaction proceeded rapidly and was completed in about 30 minutes. The solvent was removed under reduced pressure, and the residue was dissolved in ethyl acetate. The solution was washed with water and saturated brine, and then dried. The solvent was removed under reduced pressure and 19 g of the crude product was obtained. The product was purified with a silica gel column flash chromatograph employing hexane/ethyl acetate (2:1) as an eluent to give 11 g of the product (1'). Structural analysis by ¹HNMR (JEOL JNM-PMX60, in deuteriochloroform as δ (ppm)): 6.6–7.9 (17H, m, phenyl of the dimethoxytrityl group, phenyl of the nitrophenyl); 5.4 (1H, t, methine); 3.9 (2H,d, methylene); 3.7 (6H, s, methyl of the dimethoxytrityl group); 3.3–3.6 (4H, m, methylene of the cyanoethoxy group); 2.3 (2H, t, methine of the isopropyl group); 1.3 (12H, d, methyl of the isopropyl group). Mass spectrometry (SHIMAZU/KRATOS KOMPACT MALDI IV): 669.51; Calcd: 669.76.

Synthesis of Linear oligonucleotides

5'-pCGCAAGCTTC-X-GCCAAGCGCGCAATTAACCCCTCAAACCGC-3' (2),

5'-pCGCAAGCTTCGCCAAGCGCGCAATTAACCCCTCAAACCGC-3' (3),

5'-biotin-GAAGCTTGCGGCGGTTTGAG-3' (4),

5'-pGCCAAGCGCGCAATTAACCCCTCAAACCGC-3' (5),

5'-pGCCAAGCGCGCAATTAACCCCTCAAACCGCCGCAAGCTTC-3' (6),

5'-pCGCAAGCTTCp-3' (7), and 5'-pCGCAAGCTTC-Y-GCCAAGCGCGCAATTAACCCCTCAAACCGC-3' (8)

were synthesized on an Applied Biosystems, Model 394 using the conventional phosphoramidite method. With respect to (2), the reagent (1) synthesized as described above (which is referred to as the group "X" in the formula) was used, and the reagent (1') synthesized as described above (which is referred to as the group "Y" in the formula) was used for (8).

A phosphoric acid group was further appended to the 5'-end of Oligonucleotides (2), (3), (5), (6), and (7) on the DNA autosynthesizer using the phosphoramidite method. Biotin was further appended to the 5'-end of Oligonucleotide (4) on the DNA autosynthesizer using the phosphoramidite method.

The resulting oligonucleotides were treated with ammonia (30% $NH_4OH$ 1 hour at room temperature, and 55° C., 8 hours) to carry out after treatments such as removal of protecting groups and further after they were roughly purified with Oligo-PakSP (available from Milipore Inc.) (only with respect to (4)), the oligonucleotides were desalted with a NAP-25 column (available from Pharmacia Inc.) and concentrated under centrifugation.

The purification of the oligonucleotides were respectively carried out by HPLC using an ion exchange column or by reverse phase HPLC (LC-10A available from Shimazu Manufacturing Co. Ltd.) In a similar manner, a 70-mer oligonucleotide 5'-pCGCAAGCTTCGCCCGCACCGATCGC-X-GCCAAGCGCGCAATTAACCCCCTTCCCAACAGTTGCTCAAACCGC-3' was synthesized with a DNA autosynhtesizer and purified.

Preparation of Cyclic oligonucleotides

Linear Oligonucleotide (2), (3), or (8) 10 μl (100 pmol/μμl), 10 μl of (4) as the template for cyclization, 8930 μl of ultrapurified water, and 1 ml of T4 DNA Ligase buffer (available from Takara Shuzo Co. Ltd.) were mixed and allowed to stand under the shielded light at 27° C. for 30 minutes. Subsequently, the mixture was allowed to stand at 16° C. for several minutes under the shielded light and with the addition of 50 μl of T4 DNA Ligase (available from Takara Shuzo Co. Ltd, 350 Unit/μl), the mixture was allowed to stand for 4 hours. After concentration under centrifugation, the mixture was desalted with a NAP-25 column, then concentrated, centrifuged again and the cyclization template was removed therefrom with magnetic beads that were coated with avidin (DYNABEADS M280 Streptavidine available from DYNAL). Purification was conducted by fractionating on a HPLC and the desired fractions were collected and desalted. The resulting cyclic oligonucleotides are referred to as (2'), (3'), and (8'), respectively. The HPLC conditions used are as follows:

Column: TOSOH TSKgel DNA-NPR 4.6 mm φ×7.5 mm;
Flow Rate: 1.0 ml/min;
Column Oven Temperature: 37° C.;
Buffer A: 20 mM Tris-HCl, pH 9;

Buffer B: 1.0M NaCl in Buffer A
Gradients: A/B (%), from 60/40 to 40/60 over 30 minutes.

The resulting cyclic oligonucleotides were analyzed by electrophoresis on a 20% polyacrylamide gel (hereinafter referred to as "PAGE") and the mobility of the linear 40-mer oligonucleotide was found to be different from that of the cyclic 40-mer cyclic oligonucleotide. It was confirmed that the cyclic oligonucleotide had slightly greater mobility than the linear oligonucleotide.

The 70-mer linear oligonucleotide synthesized as described above was also cyclized by manipulations similar to those used above to afford cyclic oligonucleotides. Analysis by PAGE affirmed that the mobility of the linear 70-mer oligonucleotide was different from that of the cyclic 70-mer oligonucleotide.

Nuclease-resistance Tests for Cyclic oligonucleotides

The resistance tests against nuclease were conducted on linear oligonucleotide (2), which was purified and which did not contain a photocleavable group, and cyclic oligonucleotide (2') (hereinafter the linear nucleotide is referred to as "Linear", and the cyclic oligonucleotide as "Circular").

The nuclease enzymes used were: (1) four kinds of exonuclease, namely Exonuclease III, Exonuclease V, Exonuclease VII, and λ Exonuclease; and (2) three kinds of endonuclease, namely S1 Nuclease, Mung Bean Nuclease, and BAL 31 Nuclease.

Figure 10:
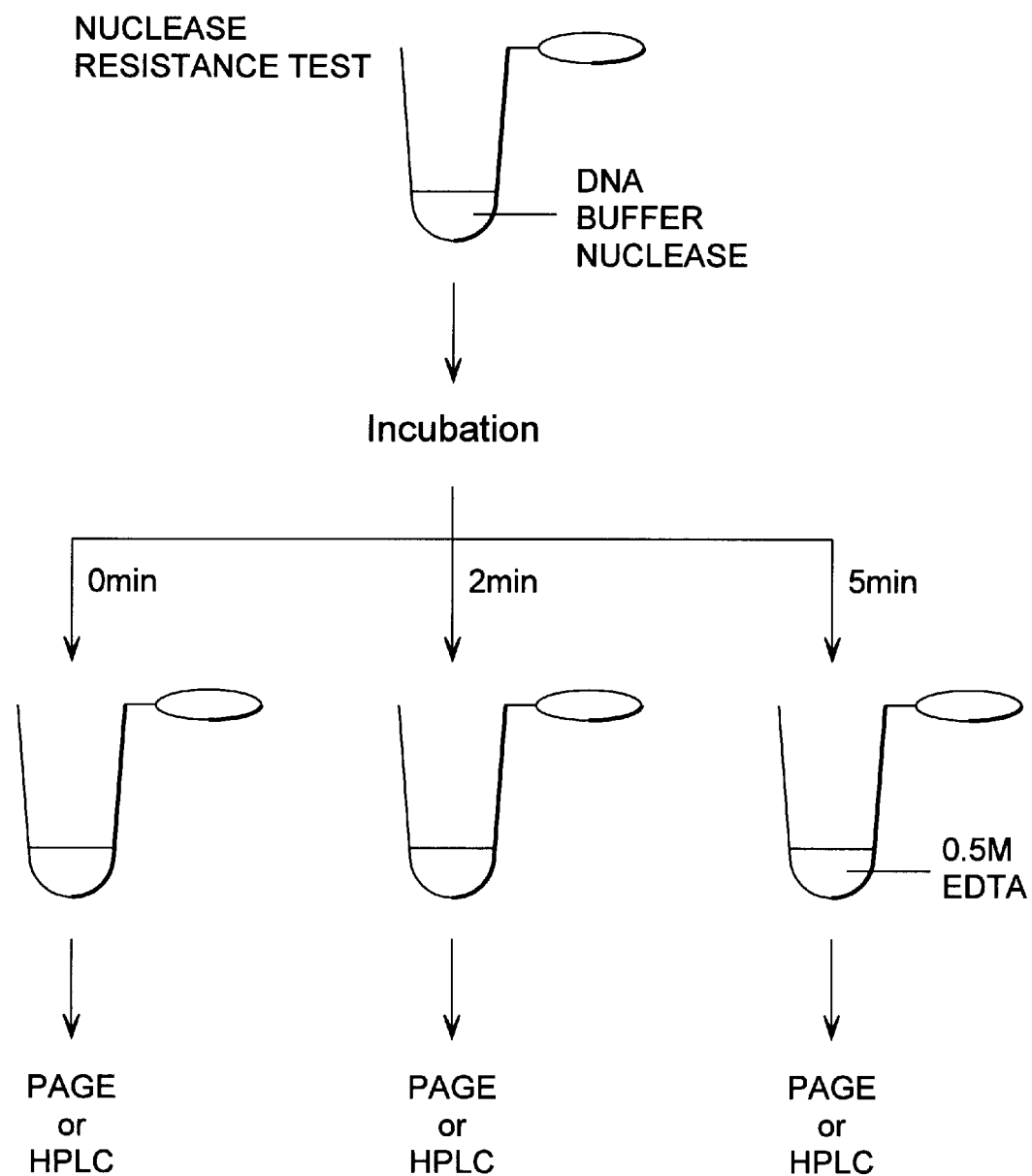
FIG. 10 illustrates an experiment protocol for the activity of resistance to nuclease with respect to cyclic or linear oligonucleotides according to the invention.

The tests were conducted by following the procedure as described below (See, FIG. 10):

(1) Exonuclease Resistance Test

Each approximately 15 pmol of oligonucleotides (both Linear and Circular) was added to 15 μl of an exonuclease reaction solution containing: Exonuclease III, 50 mM Tris-HCl (pH 8.0), 5 mM $MgCl_2$, and 10 mM 2-mercaptoethanol; Exonuclease V, 66.7 mM glycine-NaOH (pH 9.4), 30 mM $MgCl_2$, 8.3 mM 2-mercaptoethanol, and 0.5 mM ATP; Exonuclease VII, 50 mM Tris-HCl (pH 7.9), 50 mM calcium phosphate, (pH 7.6), 8.3 mM EDTA, and 10 mM 2-mercaptoethanol; and λ Exonuclease, 67 mM glycine-KOH (pH 9.4), 2.5 mM $MgCl_2$, and 0.05% BSA. To this mixture was added the enzymes (Exonuclease III 90 U; Exonuclease V 3.8 U; Exonuclease VII 5 U; and λ Exonuclease 2.5 U). After the respective reaction solutions had been incubated for 30 minutes at 37° C. in a thermostatic bath, they were run on a 20% PAGE (20 mM, 40 minutes, staining with ethidium bromide (EtBr) for 30 minutes) and the degree of decomposition of Linear or Circular was investigated.

(2) Endonuclease Resistance Test

Each approximately 150 pmol of oligonucleotides (both Linear and Circular) was added to 150 μl of an endonuclease reaction solution containing: S1 Nuclease, 30 mM sodium acetate (pH 4.6), 280 mM NaCl, and 1 mM $ZnSO_4$; Mung Bean Nuclease, 30 mM sodium acetate (pH 5.0), 100 mM NaCl, and 5% glycerol; BAL 31 Nuclease, 20 mM Tris-HCl (pH 8.0), 600 mM NaCl, 12 mM $MgCl_2$, and 1 mM EDTA. To this mixture was added the enzymes (S1 Nuclease 0.5 U; Mung Bean Nuclease 1 U; and BAL 31 Nuclease 0.2 U). The reaction solution was incubated at 37° C. (S1 and Mung Bean) or at 30° C. (BAL 31). Once the reaction started, a 50 μl aliquot was taken after periods of 0, 2, and 5 minutes, respectively and it was transferred to a fresh tube containing 5 μl of 0.5M EDTA to completely terminate the enzyme reaction.

After the completion of the reaction, the reaction solution was analyzed by HPLC (TOSOH TSK gel DNA-NPR, Solvent A: 20 mM Tris-HCl (pH 9.0), and Solvent B: 1M NaCl with a gradient of A/B being from 100/0 to 40/60 over 60 minutes in Solvent A) and the degree of decomposition of Linear or Circular was investigated. The changes observed through HPLC analysis are summarized in Table 1.

TABLE 1

| Time (min) | Area of the Parent peak (mV × sec) | Total of the peak area (40–52 min) | Ratio of the parent peak (40–52 min) | Decline of the parent peak (%) |
|---|---|---|---|---|
| S1 Nuclease | | | | |
| -Linear- | | | | |
| 0 | 195.07 | 201.68 | 96.72% | — |
| 2 | 127.82 | 178.83 | 71.47% | 26.11% |
| 5 | 66.04 | 208.51 | 31.67% | 67.26% |
| -Circular- | | | | |
| 0 | 137.77 | 138.56 | 99.43% | — |
| 2 | 79.72 | 81.91 | 97.33% | 2.11% |
| 5 | 49.96 | 54.44 | 91.77% | 7.70% |
| Mung Bean Nuclease | | | | |
| -Linear- | | | | |
| 0 | 275.52 | 281.17 | 97.99% | — |
| 2 | 205.09 | 258.38 | 79.38% | 18.99% |
| 5 | 145.43 | 287.89 | 50.52% | 48.45% |
| -Circular- | | | | |
| 0 | 183.06 | 190.16 | 96.27% | — |
| 2 | 144.50 | 153.76 | 93.98% | 2.38% |
| 5 | 96.17 | 107.98 | 89.06% | 7.49% |
| BAL31 Nuclease | | | | |
| -Linear- | | | | |
| 0 | 54.97 | 87.62 | 62.74% | — |
| 2 | 12.93 | 122.95 | 10.52% | 83.24% |
| 5 | 4.44 | 186.08 | 2.38% | 96.20% |
| -Circular- | | | | |
| 0 | 102.89 | 107.65 | 95.57% | — |
| 2 | 60.76 | 67.32 | 90.25% | 5.57% |
| 5 | 23.94 | 30.34 | 78.91% | 17.44% |

Summarizing the above results, the following general trend was recognized:

| Exonuclease | Circular | Linear |
|---|---|---|
| Exonuclease III | − | (+) |
| Exonuclease V | − | + |
| Exonuclease VII | − | + |
| λExonuclease | − | + |

| endonuclease | | |
|---|---|---|
| S1 Nuclease | complete decomposition before 15 minutes past | complete decomposition in 5 minutes |
| Mung Bean Nuclease | survives even after 30 minutes | complete decomposition in 30 minutes |
| BAL31 Nuclease | complete decomposition in 10 minutes | complete decomposition in 5 minutes |

The enzymes that were tested for their resistance activity against exonuclease did not decompose the cyclic oligonucleotides. In other words, the bands on PAGE showed no changes, and this clearly indicates that the cyclic oligonucleotides are resistant to these exonuclease enzymes.

Also, all the endonuclease enzymes that were tested for their resistance activity against endonuclease showed differences in the degree of decomposition between Linear and Circular. Accordingly, it is evident that cyclization of the oligonucleotides provides them with the resistance activity against endonuclease.

Irradiation of Linear and Cyclic Oligonucleotides Containing Photocleavable Groups Irradiation experiments were conducted on the following oligonucleotides:

Linear 40-mer Oligonucleotide (2) containing the photocleavable group X;

30-mer oligonucleotide (5) wherein the 5'-end generated upon irradiation of (2) was phosphorylated;

Cyclic 40-mer oligonucleotide (2') containing the photocleavable group X; and 40-mer Oligonucleotide (6) wherein the 5'-end generated upon irradiation of (2') was phosphorylated.

Here, since Oligonucleotide (2) comprises a 10-mer oligonucleotide and a 30-mer oligonucleotide both of which are bonded by the photocleavable group X, the irradiation causes (2) to split into the 10-mer and 30-mer. With respect to the sites cleaved by irradiation, a nitrosophenyl group remains at the 3'-end of the 10-mer product and a phosphoric acid group remains at the 5'-end of the 30-mer product.

Furthermore, when cyclic oligonucleotide (2') is subjected to irradiation, it is cut at the site cleaved photochemically to form a single linear 40-mer oligonucleotide. A nitrosophenyl group remains bonding to the 5'-end of this linear 40-mer oligonucleotide. After Oligonucleotide (2) or (2') was dissolved in a TE buffer solution at a concentration of 50 pmol/10 μl and irradiated with a xenon lamp (USHIO, 300 W, no filter, at room temperature) for 30 minutes, the solution was analyzed on a 20% PAGE.

Figure 11:
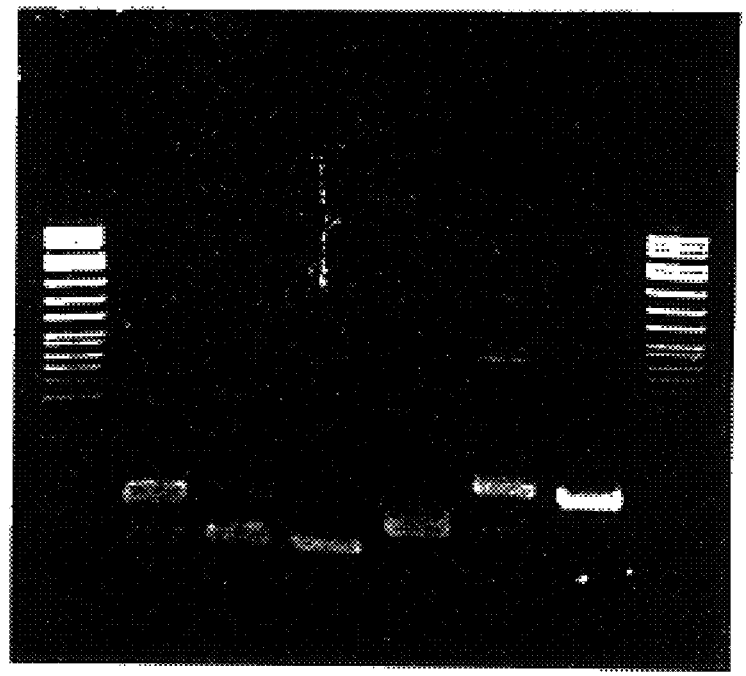
FIG. 11 illustrates a photograph demonstrating the results of polyacrylamide gel electrophoresis for the photocleavage reaction of the cyclic or linear oligonucleotides according to the invention, where Lane 1 represents a linear 40-mer sequence (2), Lane 2 represents the irradiated product of the linear 40-mer sequence (2), Lane 3 represents a synthetic 30-mer sequence (5), Lane 4 represents a cyclic 40-mer sequence (2'), Lane 5 represents the irradiated product of the cyclic 40-mer sequence (2'), and Lane 6 represents a synthetic 40-mer sequence (6).

As shown in FIG. 11, these results demonstrate that the product (Lane 2) from irradiation of Oligonucleotide (2) (Lane 1) appears at almost the same position as Oligonucleotide (5) (Lane 3) and that the product (Lane 5) from irradiation of oligonucleotide (2') (Lane 4) appears at the almost the same position as Oligonucleotide (6) (Lane 6).

Further, irradiation experiments were conducted on the following oligonucleotides:

Linear 40-mer Oligonucleotide (8) containing the photocleavable group Y;

30-mer Oligonucleotide (5) wherein the 5'-end generated upon irradiation of Oligonucleotide (2) was phosphorylated;

Cyclic 40-mer Oligonucleotide (8') containing the photocleavable group X; and 40-mer Oligonucleotide (6) wherein the 5'-end generated upon irradiation of Oligonucleotide (8') was phosphorylated.

Here, since Oligonucleotide (8) comprises a 10-mer oligonucleotide and a 30-mer oligonucleotide both of which are bonded by the photocleavable group Y, the irradiation causes oligonucleotide (8) to split into the 10-mer and 30-mer. With respect to the sites cleaved photochemically, a nitrosophenyl group remains at the 3'-end of the 10-mer product and a phosphoric acid group remains at the 5'-end of the 30-mer product.

Furthermore, when cyclic Oligonucleotide (8) is subjected to irradiation, it is cut at the site cleaved photochemically to form a single linear 40-mer oligonucleotide. A nitrosophenyl group remains bonding to the 5'-end of this linear 40-mer oligonucleotide. After Oligonucleotide (8) or (8') was dissolved in a TE buffer solution at a concentration of 50 pmol/10 μl and irradiated with a xenon lamp (USHIO, 300 W, no filter, room temperature) for 30 minutes, the solution was analyzed on a 20% PAGE.

Figure 12:
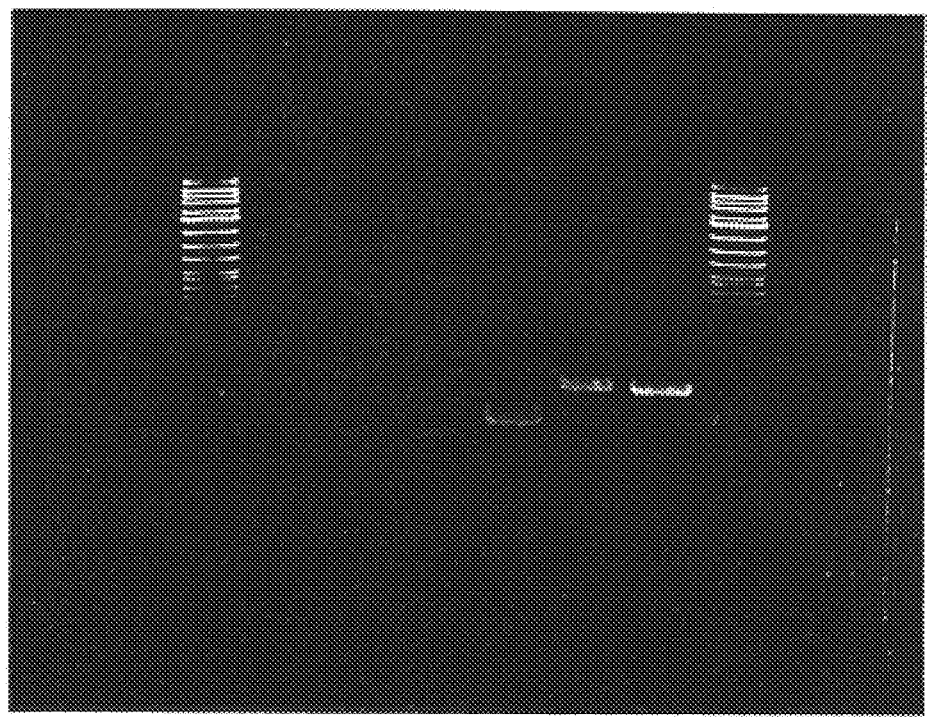
FIG. 12 illustrates a photograph demonstrating the results of polyacrylamide gel electrophoresis for the photocleavage reaction of the cyclic or linear oligonucleotides according to the invention, where Lane 1 represents a linear 40-mer sequence (8), Lane 2 represents the irradiated product of the linear 40-mer sequence (8), Lane 3 represents the synthetic 30-mer sequence (5), Lane 4 represents a cyclic 40-mer sequence (8'), Lane 5 represents the irradiated product of the cyclic 40-mer sequence (8'), and Lane 6 represents the synthetic 40-mer sequence (6).

As shown in FIG. 12, these results demonstrate that the product (Lane 2) from irradiation of oligonucleotide (8)

(Lane 1) appears at almost the same position as Oligonucleotide (5) (Lane 3) and that the product (Lane 5) from irradiation of Oligonucleotide (8') (Lane 4) appears at the almost the same position as Oligonucleotide (6) (Lane 6).

Consequently, it is evident that the irradiation causes the cleavage of the linear and cyclic oligonucleotides at their respective sites where the photoclevable groups are present (See, FIGS. 11 and 12).

Figure 13:
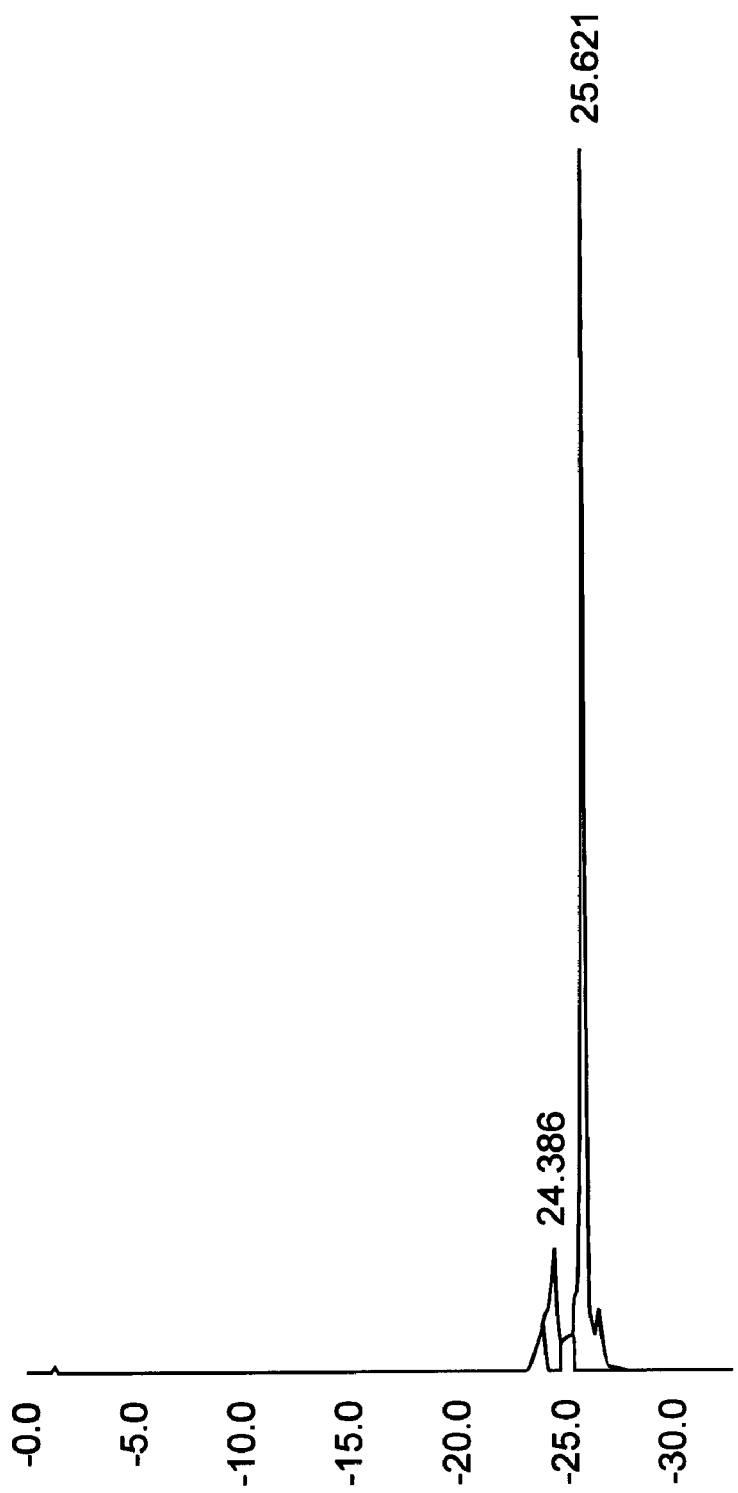
FIG. 13 illustrates the results of HPLC analysis of linear Oligonucleotide (2) prior to its irradiation.
Figure 14:
FIG. 14 illustrates the results of HPLC analysis of linear Oligonucleotide (2) after its irradiation.

The results of HPLC analysis on linear oligonucleotide (2) before and after irradiation are shown in FIGS. 13 and 14. The HPLC conditions used are as follows:

Column: TOSOH TSKgel DNA-NPR 4.6 mm φ×7.5 cm;
Flow Rate: 0.75 ml/min;
Column Oven Temperature: 37° C.;
Buffer A: 20 mM Tris-HCl, pH 9.0;
Buffer B: 1.0M NaClO$_4$ in Buffer A;
Gradients: A/B (%), from 95/5 to 65/35 over 45 minutes; and
Detection: 260 nm UV.

Figure 15:
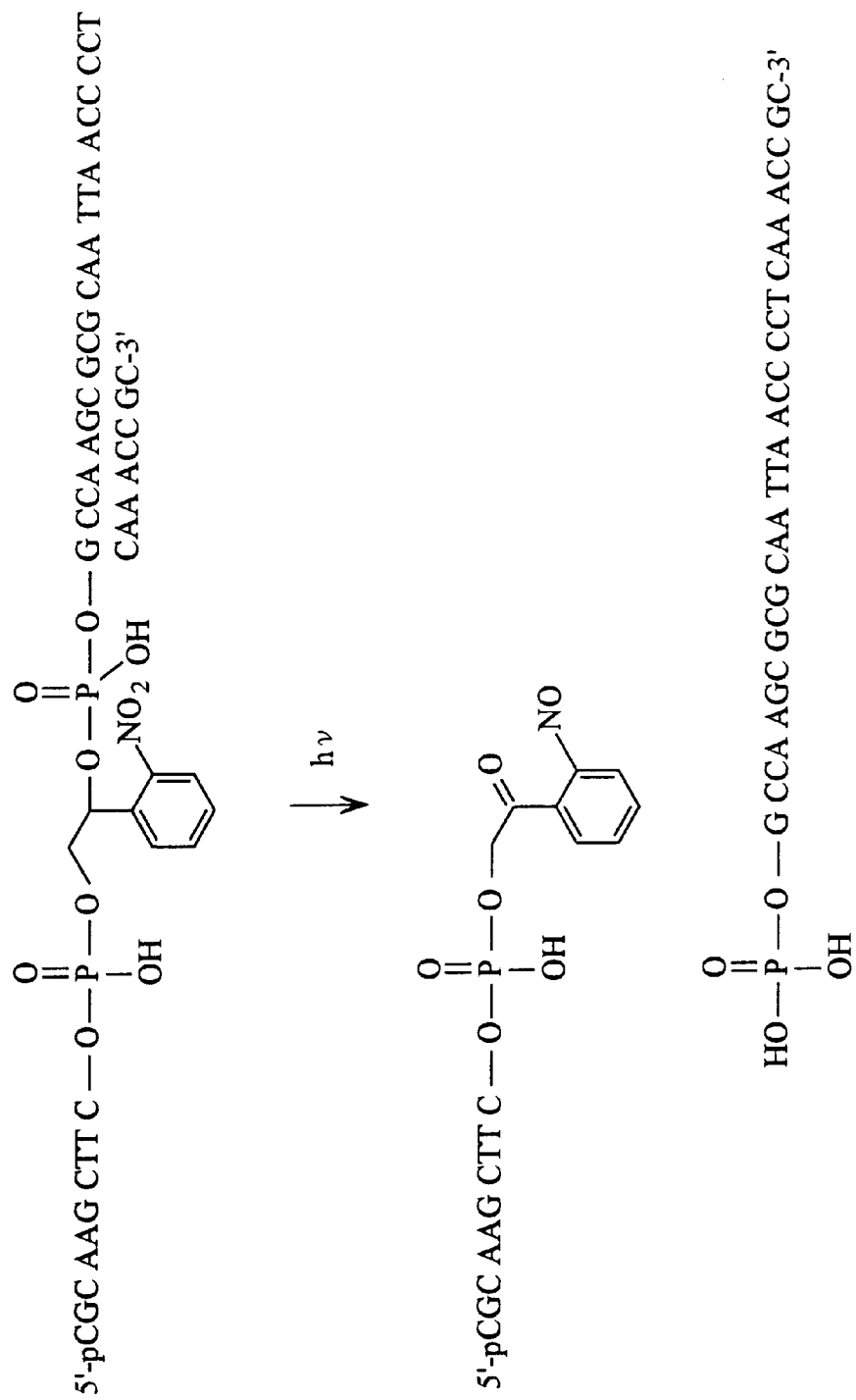
FIG. 15 illustrates the photocleavage of linear Oligonucleotide (2) by means of irradiation.
Figure 16:
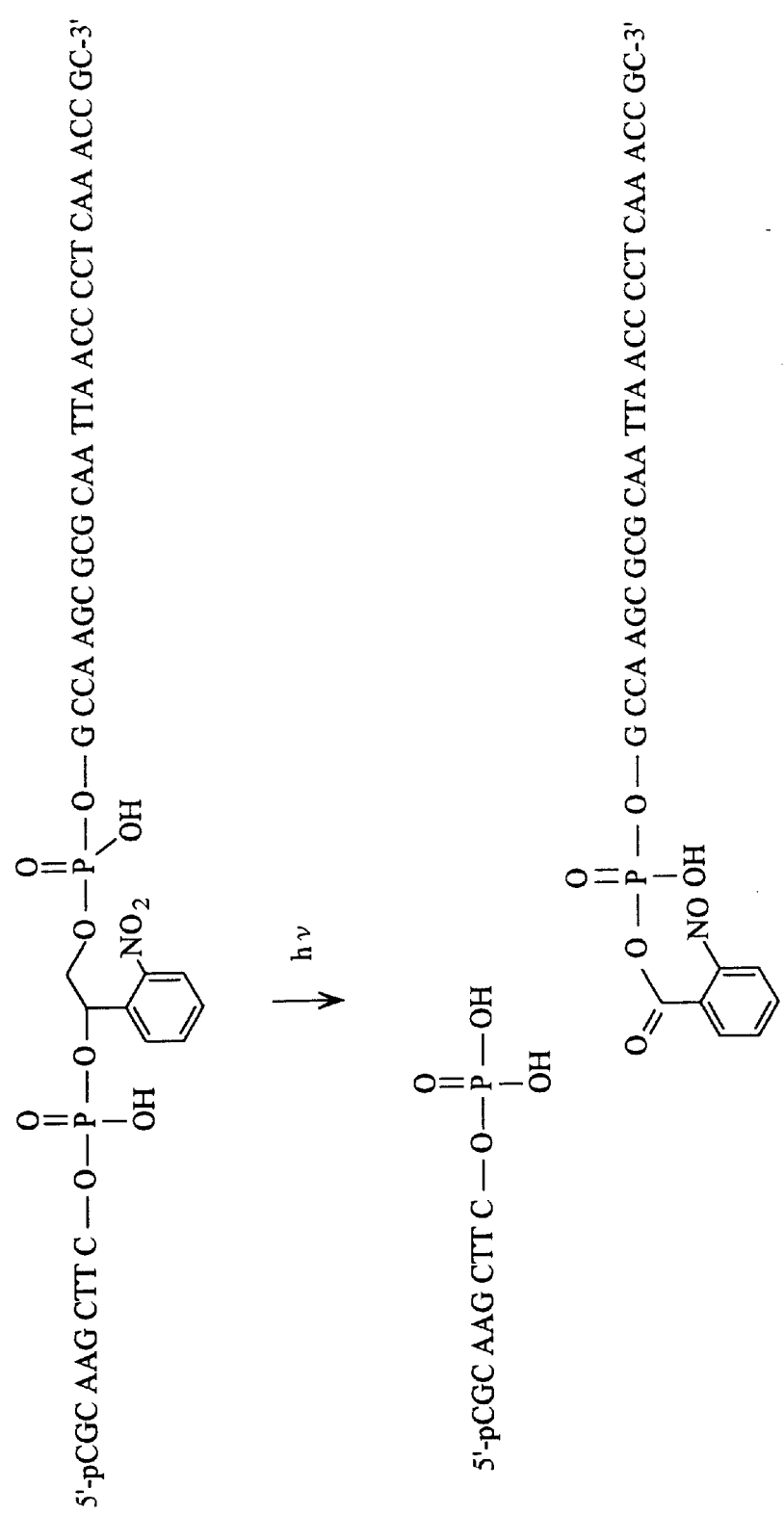
FIG. 16 illustrates the photocleavage of linear Oligonucleotide (8) by means of irradiation.

This indicates that while Oligonucleotide (2) itself displayed a single peak with the retention time of 25.621 minutes, after irradiation it displayed two peaks with the retention times of 14.744 minutes and 24.427 minutes, respectively. The peak with the retention time of 24.427 minutes coincided with the peak (24.382 minutes) of Oligonucleotide (5). Accordingly, the above results demonstrate that Oligonucleotide (2) was cleaved photochemically as shown in FIGS. 15 and 16. Likewise, Oligonucleotide (8) was cleaved photochemically as shown in FIG. 16.

The oligonucleotides synthesized in this invention are as follows: NO. 1, Length: 41, Type: nucleic acid, Strandedness: single stranded, Topology: linear, Molecule Type: DNA, Sequence Description: pCGCAAGCTTC NGCCAAGCGC GCAATTAACC CCTCAAACCG C (wherein "pC" represents cytosine the 5'-end of which is phosphorylated and "N" represents an unspecified nucleotide); NO. 2, Length: 40, Type: nucleic acid, Strandedness: single stranded, Topology: linear, Molecule Type: DNA, Sequence Description: PCGCAAGCTTC GCCAAGCGCG CAATTAACCC CTCAAACCGC; NO. 3 (with a cyclic structure), Length: 40, Type: nucleic acid, Strandedness: single stranded, Topology: cyclic, Molecule Type: DNA, Sequence Description: CGCAAGCTTC GCCAAGCGCG CAATTAACCC CTCAAACCGC; NO. 4, Length: 20, Type: nucleic acid, Strandedness: single stranded, Topology: linear, Molecule Type: DNA, Sequence Description: BiotinGAAGCTTGCG GCGGTTTGAG (wherein "BiotinG" represents biotinylated guanine); NO. 5, Length: 30, Type: nucleic acid, Strandedness: single stranded, Topology: linear, Molecule Type: DNA, Sequence Description: pGCCAAGCGCG CAATTAACCC CTCAAACCGC (wherein "pG" represents guanine the 5'-end of which is phosphorylated); NO. 6, Length: 40, Type: nucleic acid, Strandedness: single stranded, Topology: linear, Molecule Type: DNA, Sequence Description: pGCCAAGCGCG CAATTAACCC CTCAAACCGC CGCAAGCTTC (wherein "pG" represents guanine the 5'-end of which is phosphorylated); NO. 7, Length: 10, Type: nucleic acid, Strandedness: single stranded, Topology: linear, Molecule Type: DNA, Sequence Description: pCGCAAGCTTCp (wherein "pC" represents cytosine the 5'-end of which is phosphorylated and "Cp" represents cytosine the 3'-end of which is phosphorylated); NO. 8, Length: 71, Type: nucleic acid, Strandedness: single stranded, Topology: linear, Molecule Type: DNA, Feature: location: 1; method for determining the feature: E; other information: 5'-end phosphorylated, Sequence Description: CGCAAGCTTC GCCCGCACCG ATCGCNGCCA AGCGCGCAAT TAACCCCCTT CCCAACAGTT GCTCAAACCG C (wherein "N" represents an unspecified nucleotide); and NO. 9, Length: 71, Type: nucleic acid, Strandedness: single stranded, Topology: cyclic Molecule Type: DNA, Sequence Description: CGCAAGCTTC GCCCGCACCG ATCGCNGCCA AGCGCGCAAT TAACCCCCTT CCCAACAGTT GCTCAAACCG C (wherein "N" represents an unspecified nucleotide).

Interaction between Cyclic Oligonucleotide and Linear Oligonucleotide

A single stranded 40-mer oligonucleotide (target) having a complementary sequence and the sequence of: 5'-GCGGT TTGAG GGGTT AATTG CGCGC TTGGC GAAGC TTGCG-3' was used to prepare a cyclic 40-mer oligonucleotide resulting from the cyclization of the base sequence.

36 μl of the aforementioned target oligonucleotide (100 μM) and 36 μl of the aforementioned cyclic oligonucleotide (100 μM) were mixed in a total 150 μl of a solution comprising 12 μl of 10xBuffer (0.1M NaCl, 10 mM phosphate buffer, pH 7.0), 30 μl of formamide, and 36 μl of ultrapurified water. The resulting solution was subjected to annealing under the following conditions: for 5 minutes at 95° C., then for 20 minutes at 50° C., and subsequently, at room temperature).

The thus obtained solution was measured for any change in absorbance at 260 nm with temperature variations (raising from 30° C. to 85° C. at the rate of 30° C. per hour).

In comparison, a similar measurement was made using a linear, single-stranded, 40-mer oligonucleotide with the base sequence that is complementary to the aforementioned target oligonucleotide.

Temperature-dependence of absorbance was observed both for the cyclic oligonucleotide and single-stranded oligonucleotide when they were mixed with the target oligonucleotide under the conditions as described above. Here, the inflection point of the temperature-dependence curve of absorbance was taken as a melting point of the nucleotide by following the conventional method of measurement for the melting point of a nucleic acid (i.e., the temperature at which its double-strand changes to a single strand). Thus the melting point obtained was 61° C. in the case of the cyclic oligonucleotide, whereas it was 67° C. in the case of the single-stranded oligonucleotide which was used as a comparison.

These results suggest that the aforementioned 40-mer cyclic oligonucleotide strongly interacts with the target oligonucleotide as does the single-stranded oligonucleotide, and that its product has a structure similar to the formation of a normal double strand.

The formation of a stable complex arising from the interaction between the 40-mer cyclic oligonucleotide and the single-stranded oligonucleotide was ascertained by separation using an anion exchange HPLC. The HPLC conditions used are as follows:

Column: TOSOH TSKgel DNA-NPR 4.6 mm φ×7.5 cm;
Flow Rate: 0.8 ml/min;
Column Oven Temperature: 37° C.;
Buffer A: 20 mM Tris-HCl, pH 9.0;
Buffer B: 1.0M NaCl in Buffer A;
Gradients: A/B (%), from 80/20 to 20/80 over 10 minutes; and
Detection: 260 nm UV.

Figure 17:
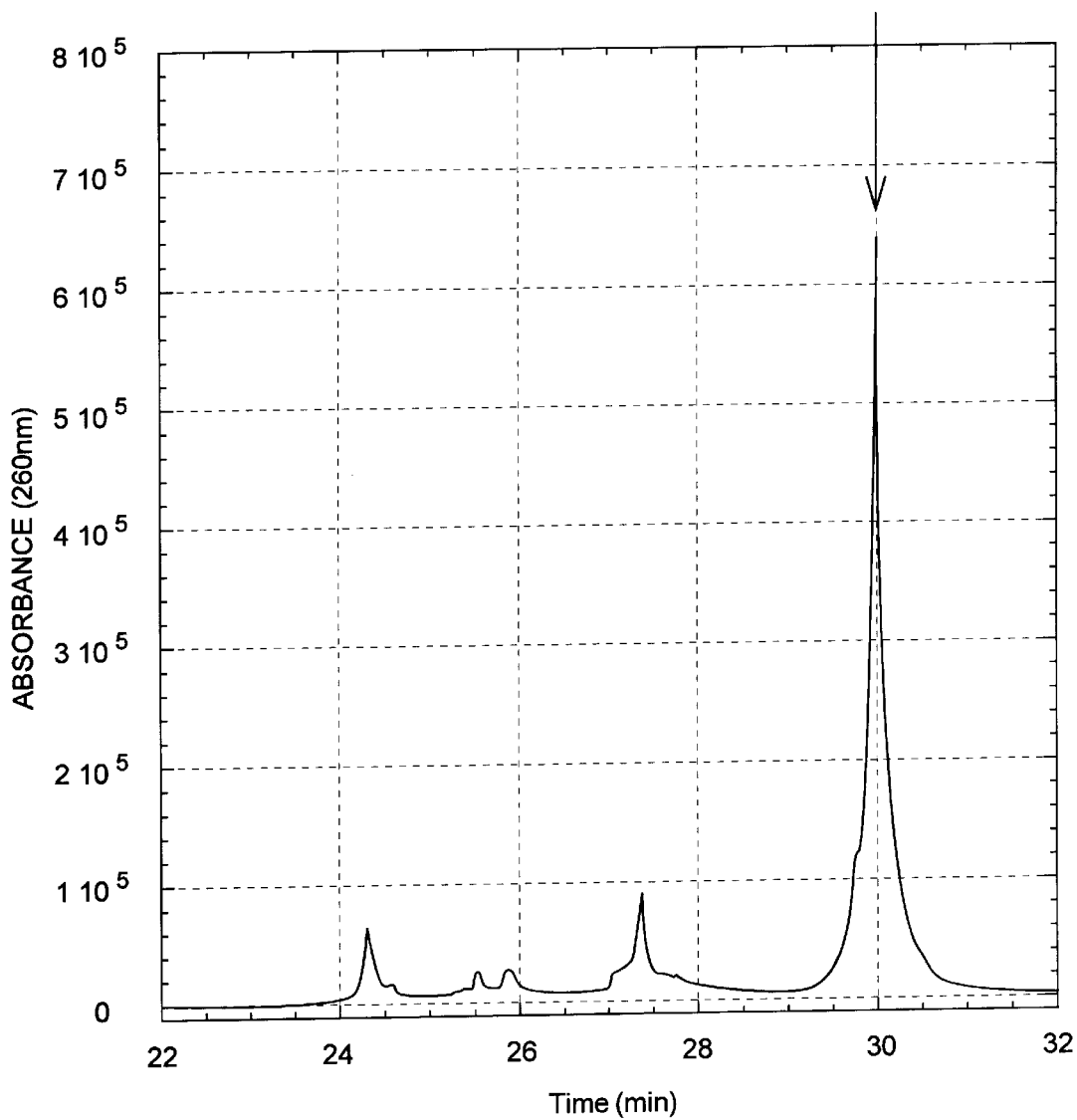
FIG. 17 illustrates the results of HPLC analysis showing a complex formed by interaction between the cyclic oligonucleotide according to the invention and the target nucleic acid.
Figure 18:
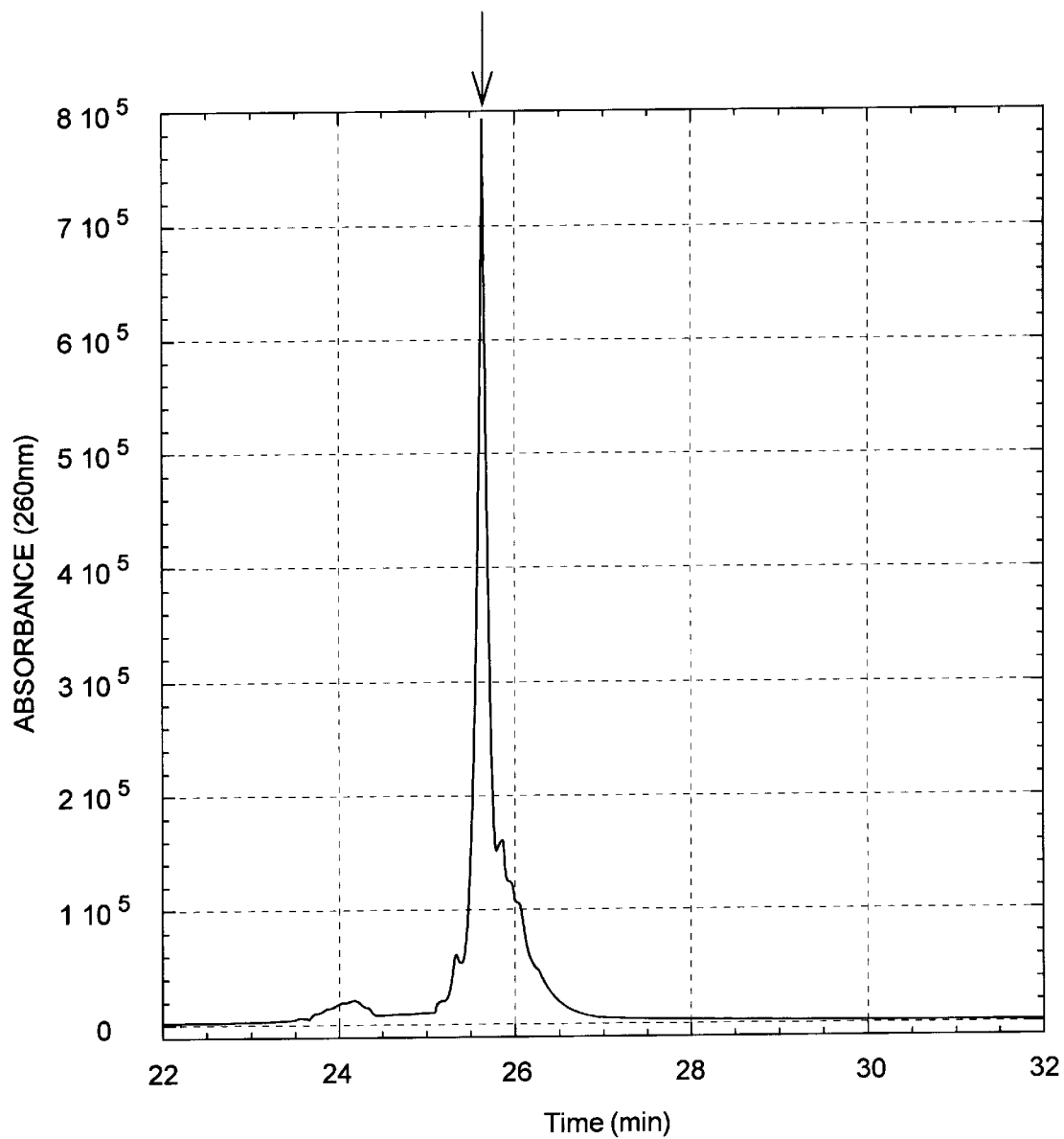
FIG. 18 illustrates the results of HPLC analysis showing a hybridized product formed by interaction between the linear oligonucleotide according to the invention and the target nucleic acid.

FIG. 17 clearly shows a peak (30 minutes) illustrative of the presence of the complex between the cyclic oligonucleotide and the target oligonucleotide at a position different from either of the target oligonucleotide (24.5 minutes) and the cyclic oligonucleotide (24.3 minutes). In addition, FIG. 18 shows a peak (25.3 minutes) resulting from a hybrid product of the target oligonucleotide and the cyclic oligonucleotide at a position different from either of the target oligonucleotide (24.5 minutes) and the single-stranded oligonucleotide (24.1 minutes). It is suggested that the difference in retention time reflects a difference between the ionic character due to a structure in solution resulting from the complex between the target oligonucleotide and the cyclic oligonucleotide and the ionic character due to a structure resulting from the hybrid product (with the formation of a complete double-strand) between the target oligonucleotide and the cyclic oligonucleotide.

INDUSTRIAL APPLICABILITY

The photocleavable cyclic oligonucleotide according to this invention, after having been introduced in vivo, is hardly susceptible to the nuclease decomposition reaction owing to its cyclic structure and thus it is capable of diffusing toward the predetermined sites in vivo with sufficient time. Moreover, by being irradiated with the light at an appropriate wavelength after a predetermined period of time, the photocleavable group as described above is cleaved photochemically, thus cutting the predetermined bond. This permits the oligonucleotide that was cyclic to be a linear oligonucleotide which is then able to hybridize with DNA or RNA to be targeted.

Accordingly, when the photocleavable cyclic oligonucleotide having the structure according the invention is introduced in vivo and, after a period of time sufficient to diffuse toward arbitrary sites (e.g., a specific cell or site), the specific sites are irradiated, and an antisense oligonucleotide is expressed only when and where the irradiation was carried out: this enables gene control.

We claim:

1. A circular oligonucleotide comprising at least one photocleavable group, wherein the oligonucleotide is intramolecularly bonded by the photocleavable group.

2. The circular oligonucleotide according to claim 1, wherein the photocleavable group has the following structure:

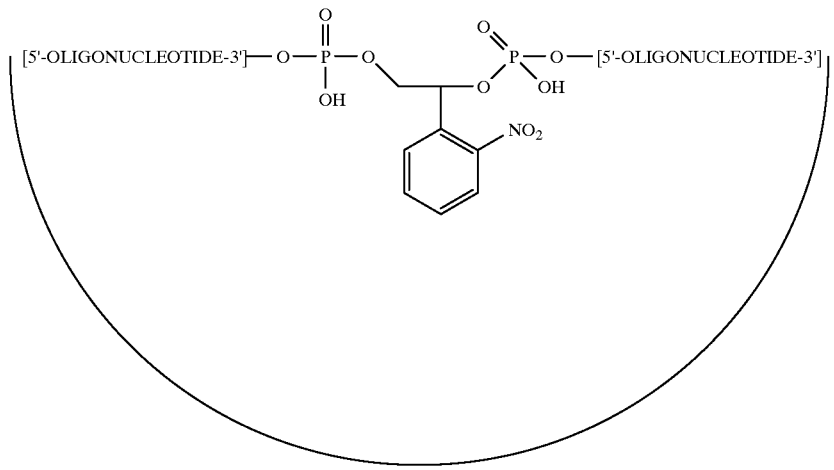

3. The circular oligonucleotide according to claim 1, wherein the photocleavable group has the following structure:

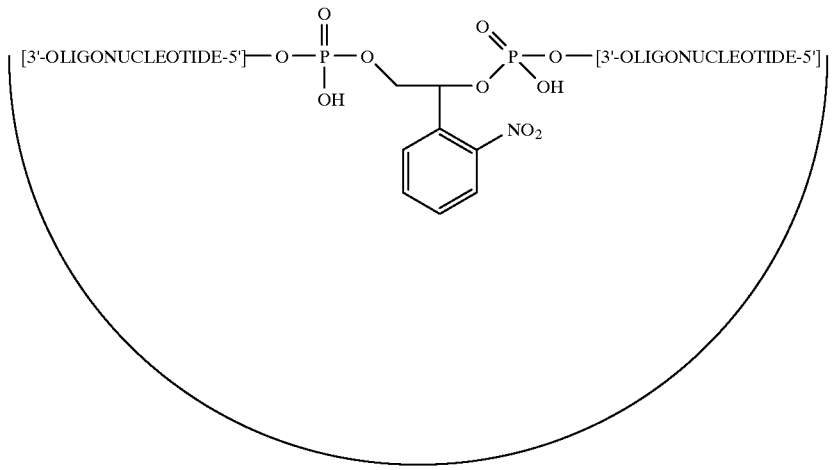

4. The circular oligonucletide according to claim 1, wherein the oligonucleotide comprises from 10 to 200 bases.

5. The circular oligonucleotide according to claim 1, wherein the oligonucleotide comprises from 30 to 100 bases.

6. The circular oligonucleotide according to claim 1, wherein the oligonucleotide is provided with a first base sequence complementary to at least a partial base sequence of a target nucleic acid upon cleavage of the photocleavable group.

7. The circular oligonucleotide according to claim 1, wherein the oligonucleotide is provided with a first base sequence complementary to at least a partial base sequence of a target nucleic acid upon cleavage of the photocleavable group and with a second base sequence through which the oligonucleotide hybridizes with the target nucleic acid.

8. The circular oligonucleotide according to claim 1, wherein the oligonucleotide is provided with a first base sequence of at least about 15 bases that hybridizes with at least a partial base sequence of a target nucleic acid upon cleavage of the photocleavable group.

9. The circular oligonucleotide according to claim 1, wherein the oligonucleotide is provided with a first base sequence of at least about 15 bases that hybridizes with at least a partial base sequence of a target nucleic acid upon cleavage of the photocleavable group and with a second base sequence through which the oligonucleotide hybridizes with the target nucleic acid.

10. The circular oligonucleotide according to claim 1, wherein the oligonucleotide is provided with a means for hybridizing to at least a partial base sequence of a target nucleic acid upon cleavage of the photocleavable group.

11. The circular oligonucleotide according to claim 1, wherein the oligonucleotide is provided with a first means for hybridizing to at least a partial base sequence of a target nucleic acid upon cleavage of the photocleavable group and with a second means for hybridizing with the target nucleic acid.

* * * * *

```
                           SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (ix) FEATURE:
         (D) OTHER INFORMATION: 5'-end phosphorylated; "N" represents a
             group bonding 1 or 2-(o-nitrophenyl)
             ethanediol and phosphoric ester (xi) SEQUENCE DESCRIPTION: SEQ ID NO:1:

CGCAAGCTTC NGCCAAGCGC GCAATTAACC CCTCAAACCG C                              41

(2) INFORMATION FOR SEQ ID NO:2:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (ix) FEATURE:
         (D) OTHER INFORMATION: 5'-end phosphorylated (xi) SEQUENCE DESCRIPTION: SEQ ID NO:2:

CGCAAGCTTC GCCAAGCGCG CAATTAACCC CTCAAACCGC                                40
```

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: cyclic (ii) MOLECULE TYPE: DNA (iii) HYPOTHETICAL: NO (iv) ANTI-SENSE: NO (xi) SEQUENCE DESCRIPTION: SEQ ID NO:3:

CGCAAGCTTC GCCAAGCGCG CAATTAACCC CTCAAACCGC          40

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (D) OTHER INFORMATION: 5'-end biotinylated (xi) SEQUENCE DESCRIPTION: SEQ ID NO:4:

GAAGCTTGCG GCGGTTTGAG          20

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (D) OTHER INFORMATION: 5'-end phosphorylated (xi) SEQUENCE DESCRIPTION: SEQ ID NO:5:

GCCAAGCGCG CAATTAACCC CTCAAACCGC          30

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:

(D) OTHER INFORMATION: 5'-end phosphorylated (xi) SEQUENCE DESCRIPTION: SEQ ID NO:6:

GCCAAGCGCG CAATTAACCC CTCAAACCGC CGCAAGCTTC                          40

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (D) OTHER INFORMATION: 5'-end of the first cytosine and 3'-end
            of the tenth cytosine phosphorylated (xi) SEQUENCE DESCRIPTION: SEQ ID NO:7:

CGCAAGCTTC                                                           10

(2) INFORMATION FOR SEQ ID NO:8:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (D) OTHER INFORMATION: 5'-end phosphorylated; "N" represents a
            group bonding 1 or 2-(o-nitrophenyl)
            ethanediol and phosphoric ester (xi) SEQUENCE DESCRIPTION: SEQ ID NO:8:

CGCAAGCTTC GCCCGCACCG ATCGCNGCCA AGCGCGCAAT TAACCCCCTT CCCAACAGTT    60

GCTCAAACCG C                                                         71

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: cyclic (ii) MOLECULE TYPE: DNA (iii) HYPOTHETICAL: NO (iv) ANTI-SENSE: NO (ix) FEATURE:
        (D) OTHER INFORMATION: "N" represents a group bonding 1 or
            2-(o-nitrophenyl) ethanediol and
            phosphoric ester (xi) SEQUENCE DESCRIPTION: SEQ ID NO:9:

CGCAAGCTTC NGCCAAGCGC GCAATTAACC CCTCAAACCG C                        41

(2) INFORMATION FOR SEQ ID NO:10:

(i) SEQUENCE CHARACTERISTICS:
        (A) LENGTH: 70 base pairs
        (B) TYPE: nucleic acid
        (C) STRANDEDNESS: single
        (D) TOPOLOGY: cyclic (ii) MOLECULE TYPE: DNA (iii) HYPOTHETICAL: NO (iv) ANTI-SENSE: NO (xi) SEQUENCE DESCRIPTION: SEQ ID NO:10:

```
CGCAAGCTTC GCCCGCACCG ATCGCGCCAA GCGCGCAATT AACCCCCTTC CCAACAGTTG    60

CTCAAACCGC                                                           70
```

(2) INFORMATION FOR SEQ ID NO:11:

(i) SEQUENCE CHARACTERISTICS:
        (A) LENGTH: 71 base pairs
        (B) TYPE: nucleic acid
        (C) STRANDEDNESS: single
        (D) TOPOLOGY: cyclic (ii) MOLECULE TYPE: DNA (iii) HYPOTHETICAL: NO (iv) ANTI-SENSE: NO (ix) FEATURE:
        (D) OTHER INFORMATION: "N" represents a group bonding 1 or
            2-(o-nitrophenyl) ethanediol and
            phosphoric ester (xi) SEQUENCE DESCRIPTION: SEQ ID NO:11:

```
CGCAAGCTTC GCCCGCACCG ATCGCNGCCA AGCGCGCAAT TAACCCCCTT CCCAACAGTT    60

GCTCAAACCG C                                                         71
```